(12) United States Patent
Deisseroth et al.

(10) Patent No.: US 10,641,782 B2
(45) Date of Patent: May 5, 2020

(54) METHODS FOR VISUALIZATION AND QUANTIFICATION OF FIBER-LIKE STRUCTURES

(71) Applicant: The Board of Trustees of the Leland Stanford Junior University, Stanford, CA (US)

(72) Inventors: Karl A. Deisseroth, Stanford, CA (US); Li Ye, Mountain View, CA (US); Jennifer McNab, Stanford, CA (US); Qiyuan Tian, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 63 days.

(21) Appl. No.: 16/301,086

(22) PCT Filed: May 24, 2017

(86) PCT No.: PCT/US2017/034314
§ 371 (c)(1),
(2) Date: Nov. 13, 2018

(87) PCT Pub. No.: WO2017/205531
PCT Pub. Date: Nov. 30, 2017

(65) Prior Publication Data
US 2019/0187161 A1    Jun. 20, 2019

Related U.S. Application Data

(60) Provisional application No. 62/341,379, filed on May 25, 2016.

(51) Int. Cl.
*G01N 33/92* (2006.01)
*G02B 21/36* (2006.01)
(Continued)

(52) U.S. Cl.
CPC ........... *G01N 33/92* (2013.01); *A61B 5/0059* (2013.01); *G01N 33/48* (2013.01); *G02B 21/367* (2013.01);
(Continued)

(58) Field of Classification Search
CPC .... G01N 33/92; G01N 33/48; G01N 33/5026; G01N 33/5058; A61B 5/0042;
(Continued)

(56) References Cited

U.S. PATENT DOCUMENTS 8,852,614 B2    10/2014 Frank et al.
2010/0055733 A1    3/2010 Lutolf et al.
(Continued)

FOREIGN PATENT DOCUMENTS

WO    WO 2014025392    2/2014

OTHER PUBLICATIONS

Behrens, et al. (2007) "Probabilistic Diffusion Tractography with Multiple Fibre Orientations: What Can we Gain?", NeuroImage 34(1): 144-155.
(Continued)

*Primary Examiner* — Tri T Ton
(74) *Attorney, Agent, or Firm* — Edward J. Baba; Bozicevic, Field & Francis LLP

(57) ABSTRACT

Aspects of the present disclosure include a method for visualizing a fiber-like structure in a biological specimen, the method comprising: clearing the biological specimen comprising a fiber-like structure, wherein the fiber-like structure is detectably labeled; illuminating the cleared biological specimen with two light sheets from a first side and a second side to produce an image volume, wherein the second side is opposite to the first side and wherein the image volume comprises a representation of the fiber-like structure; defining a plurality of voxels within the represen-
(Continued)

tation of the fiber-like structure; processing each of the plurality of voxels to estimate a plurality of principal fiber-like structure orientations; and defining a starting point on the representation of the fiber-like structure and propagating a plurality of streamlines from the starting point, according to the plurality of principal fiber-like structure.

23 Claims, 6 Drawing Sheets

(51) Int. Cl.
    *A61B 5/00*     (2006.01)
    *G06T 7/13*     (2017.01)
    *G01N 33/48*     (2006.01)

(52) U.S. Cl.
    CPC ............. *G06T 7/13* (2017.01); *A61B 5/0042* (2013.01); *G06T 2207/30016* (2013.01)

(58) Field of Classification Search
    CPC ............... A61B 5/0059; G02B 21/367; G06T 2207/30016; G06T 7/13
    USPC .................................................. 356/614–640
    See application file for complete search history.

(56) References Cited

U.S. PATENT DOCUMENTS

| | | |
|---|---|---|
| 2012/0280686 A1 | 11/2012 | White et al. |
| 2014/0099659 A1 | 4/2014 | Keller |
| 2014/0294270 A1 | 10/2014 | Schneider et al. |
| 2017/0068086 A1 | 3/2017 | Tomer et al. |

OTHER PUBLICATIONS

Bevis and Glick. (2002) "Rapidly Maturing Variants of the Discosoma Red Fluorescent Protein (DsRed)", Nat. Biotechnol. 20:83-87.

Bigun and Granlund (1987) "Optimal Orientation Detection of Linear Symmetry.In: Proceedings of the IEEE First International Conference on Computer Vision", London, Great Britain pp. 433-438.

Budde and Annese (2013) "Quantification of Anisotropy and Fiber Orientation in Human Brain Histological Sections", Frontiers in Integrative Neuroscience 7(3):1-7.

Budde and Frank, (2012) "Examining Brain Microstructure Using Structure Tensor Analysis of Histological Sections", NeuroImage 63:1-10.

Guenthner, et al. (2013) "Permanent Genetic Access to Transiently Active Neurons via TRAP: Targeted Recombination in Active Populations", Neuron 78(5):773-784.

Hern and Hubbell (1998) "Incorporation of Adhesion Peptides into Nonadhesive Hydrogels Useful for Tissue Resurfacing", J. Biomed. Mater. Res. 39(2):266.

Huh and Bae (1999) "Synthesis and Characterization of Poly (Ethylene Glycol)/Poly (L-Lactic Acid) Alternating Multiblock Copolymers", Polymer 40:6147-6155.

Johnson and Hansen (2004) "Diffusion Tensor MRI Visualization", Visualization Handbook 317-330.

Kass and Witkin (1987) "Analyzing Oriented Patterns", Computer Vision, Graphics and Image Processing 37:362-385.

Khan, et al., (2015) "3D Structure Tensor Analysis of Light Microscopy Data for Validating Diffusion MRI", NeuroImage 111:192-203.

Lee, et al. (2010) "Hydrophobic Nanoparticles Improve Permeability of Cell-Encapsulating Poly(Ethylene Glycol) Hydrogels While Maintaining Patternability", Proc. Natl. Acad. Sci. 107, 20709-20714.

Matz, et al. (1999) "Fluorescent Proteins from Nonbioluminescent Anthozoa Species", Nature Biotechnology. 17:969-973.

Mori, et al. (1999) "Three Dimensional Tracking of Axonal Projections in the Brain by Magnetic Resonance Imaging", Annals of Neurology 45:265-269.

Nagai, et al. (2002) "A Variant of Yellow Fluorescent Protein with Fast and Efficient Maturation for Cell-Biological Applications", Nat. Biotechnol. 20(1):87-90.

Nguyen and Daugherty (2005) "Evolutionary optimization of fluorescent proteins for intracellular FRET", Nat Biotechnol. 23(3):355-360.

Rizzo, et al. (2004) "An Improved Cyan Fluorescent Protein Variant Useful for FRET", Rizzo, Nat Biotechnol. 22(4):445-9.

Shaner, et al. (2005) "A Guide to Choosing Fluorescent Proteins", Nat. Methods. 2(12):905-909.

Shkrob, et al. (2005) "Far-Red Fluorescent Proteins Evolved from a Blue Chromoprotein from Actinia Equina", Biochem J. 392(Pt 3):649-654.

Tainaka, et al. (2014) "Whole-Body Imaging with Single-Cell Resolution by Tissue Decolorization", Cell 159:911-924.

Wang, et al. (2004) "Evolution of New Nonantibody Proteins via Iterative Somatic Hypermutation", PNAS USA 101 (48): 16745-16749.

Wang, et al. (2015) "Structure Tensor Analysis of Serial Optical Coherence Scanner Images for Mapping Fiber Orientations and Tractography in the Brain", Journal of Biomedical Optics 20(3):036003 pp. 1-11.

West and Hubbell (1999) "Polymeric Biomaterials with Degradation Sites for Proteases Involved in Cell Migration, Polymeric Biomaterials with Degradation Sites for Proteases Involved in Cell Migration", Macromolecules, 32:241-244.

Wiedenmann, et al. (2002) "A Far-Red Fluorescent Protein with Fast Maturation and Reduced Oligomerization Tendency from Entacmaea Quadricolor Anthozoa, Actinaria", Proc Natl Acad Sci USA 99(18):11646-11651.

METHODS FOR VISUALIZATION AND QUANTIFICATION OF FIBER-LIKE STRUCTURES

CROSS-REFERENCE TO RELATED APPLICATIONS

This application claims the benefit of U.S. Provisional Patent Application No. 62/341,379 filed May 25, 2016, which application is incorporated herein by reference in its entirety.

BACKGROUND

The many individual regions and layers of the mammalian prefrontal cortex are known to contain cells with a rich diversity of activity patterns. Indeed, otherwise-indistinguishable populations of principal cells exhibiting profoundly distinct changes in activity in response to the same task or stimulus have been characterized by electrophysiological recording and cellular-resolution fluorescence $Ca^{2+}$ imaging. At the same time, datastreams of anatomical and molecular information on prefrontal cell typology have emerged from a variety of methods, also pointing toward rich cellular diversity of principal excitatory neurons. Together these findings have highlighted the morphological, wiring, and electrophysiological diversity of principal neurons even within individual layers and subregions.

The mapping and correspondences among different domains of diversity (e.g., activity during behavior, long-range wiring, and molecular phenotype) has fundamental implications for elucidating the cellular logic of prefrontal cortex function; moreover, differences in wiring, role in behavior, and molecular signatures among differentially-responsive cells could provide insight into the mechanisms of action of current neuromodulation therapies, and perhaps even lay the foundation for developing new kinds of cell-targeted disease treatment. The present disclosure provides an approach to at least quantify long-range anatomy, molecular signatures, and causal impact of prefrontal cortical cells to assess the unique and non-stereotyped nature of the mammalian nervous system.

SUMMARY

Aspects of the present disclosure include a method for visualizing a fiber-like structure in a biological specimen, the method comprising: clearing the biological specimen comprising a fiber-like structure, wherein the fiber-like structure is detectably labeled; illuminating the cleared biological specimen with two light sheets from a first side and a second side to produce an image volume, wherein the second side is opposite to the first side and wherein the image volume comprises a representation of the fiber-like structure; defining a plurality of voxels within the representation of the fiber-like structure; processing each of the plurality of voxels to estimate a plurality of principal fiber-like structure orientations; and defining a starting point on the representation of the fiber-like structure and propagating a plurality of streamlines from the starting point, according to the plurality of principal fiber-like structure orientations, to visualize the fiber-like structure.

In other aspects, the method includes where processing each of the plurality of voxels comprises: identifying a plurality of image intensity gradients within a predetermined vicinity of the voxel, and determining a structure tensor using the plurality of image intensity gradients; and estimating a principal fiber-like structure orientation from the structure tensor.

In other aspects, the method includes where the clearing comprises using a CLARITY-based method. In some cases, the clearing method includes using an electrophoresis or perfusion-based method.

In other aspects, the method includes where the clearing comprises substantially removing a plurality of cellular components from the biological specimen. In some cases the plurality of cellular components comprises lipids.

In other aspects, the method includes where each of the plurality of image intensity gradients indicate an edge of the fiber-like structure.

In other aspects, the method includes where each streamline of the plurality of streamlines terminates if a streamline makes a sharp turn. In some cases, the sharp turn is at an angle larger than a predetermined threshold. In some cases, each streamline of the plurality of streamlines terminates if the streamline propagates outside of a predetermined area. In some cases, each streamline of the plurality of streamlines terminates if the streamline comes into contact with itself, e.g. circles in on itself. In some cases each streamline of the plurality of streamlines terminates once a streamline reaches a specific region of interest, e.g. a predetermined region of interest.

In other aspects, the method includes where the principal fiber-like structure orientation is defined as a tertiary eigenvector of the structure tensor. In some cases, the structure tensor is a three-dimensional structure tensor. In some cases, the structure tensor is defined as a function comprising a Gaussian weighing function.

In other aspects, the method includes where the number of streamlines in the plurality of streamlines is used to measure a physical characteristic of the fiber-like structure. In some cases, the number of streamlines in the plurality of streamlines is used to measure the diameter of the fiber-like structure. In some cases, the number of streamlines in the plurality of streamlines is used to measure the size of the fiber-like structure.

In other aspects, the method includes where the biological specimen is a whole mammalian brain, a whole spinal cord, or other organ that comprises a fiber-like structure. In some cases, the fiber-like structure is a neural projection, a peripheral nerve, or a blood vessel.

In other aspects, the method includes where the detectably labeled fiber-like structure is labeled via stereotaxic injection, or genetic expression.

Aspects of the instant disclosure include a method for visualizing a fiber-like structure in a biological specimen of a subject animal exposed to a stimulant, the method comprising: delivering a stimulant to the subject animal; isolating the biological specimen of the subject animal; processing the biological specimen of the subject animal according to any previous method to visualize the fiber-like structure.

In other aspects, the method includes where the stimulant is amphetamine, caffeine, ephedrine, 3,4-methylenedioxymethamphetamine (MDMA), methylenedioxypyrovalerone (MDPV), prolintane, mephedrone, methamphetamine, nicotine, phenylpropanolamine, propylhexedrine, dimethylamylamine, pseudoephedrine, cathinone, or cocaine. In some cases, the stimulant generates a rewarding or aversive experience in the subject animal. In some cases, the stimulant is a physical stimulant. In some cases, the physical stimulant is pain.

Aspects of the present disclosure include a method for screening a candidate agent for the ability to modulate the patterning of a first fiber-like structure in a biological specimen of a first subject animal, the method comprising: administering the candidate agent to the subject animal; isolating the biological specimen of the subject animal; and processing the biological specimen of the subject animal according to any previous method to visualize the first fiber-like structure, wherein a change in the patterning of the first fiber-like structure in the biological specimen of the first subject animal as compared to the patterning of a second fiber-like structure in a biological specimen isolated from a second subject animal that has not been administered the candidate agent indicates that the candidate agent modulates the patterning of a fiber-like structure in a biological specimen of a subject animal.

In other aspects, the method includes where the change in the patterning of the fiber-like structure comprises an increased, or decreased number of streamlines.

In other aspects, the method includes where the first and second subject animals suffer from a pathological condition, wherein the pathological condition affects the patterning of the first and second fiber-like structures. In some cases, the pathological condition is a neurological condition.

In other aspects, the method includes where the candidate agent decreases the effect of the pathological condition on the patterning of the first and second fiber-like structures.

In other aspects, the method includes where a stimulant has been delivered to the first and second subject animals, and wherein the candidate agent increases or decreases the effect of the stimulant.

In other aspects, the method includes where the stimulant is amphetamine, caffeine, ephedrine, 3,4-methylenedioxymethamphetamine (MDMA), methylenedioxypyrovalerone (MDPV), prolintane, mephedrone, methamphetamine, nicotine, phenylpropanolamine, propylhexedrine, dimethylamylamine, pseudoephedrine, cathinone, or cocaine. In some cases, the stimulant generates a rewarding or aversive experience in the subject animal. In some cases, the stimulant is pain.

Aspects of the instant disclosure include a system for visualizing a fiber-like structure in a biological specimen, the system comprising: a memory; and a processor coupled to the memory and configured to execute instructions stored therein, the instructions comprising instructions for visualizing a first fiber-like structure in a biological specimen isolated from a first subject animal according to any previous method.

In other aspects, the system further includes: instructions for visualizing a second fiber-like structure in a biological specimen according to any previous method, wherein the biological specimen is isolated from a second subject animal, and wherein the second subject animal has been administered a stimulant; instructions to analyze the first and second fiber-like structures; and instructions to compare the first and second fiber-like structures.

In other aspects, the system further includes: instructions for visualizing a second fiber-like structure in a biological specimen according to the method of any previous claim, wherein the biological specimen is isolated from a second subject animal, and wherein the second subject animal has been administered a candidate agent; instructions to analyze the first and second fiber-like structures; and instructions to compare the first and second fiber-like structures.

DEFINITIONS

Figure 1:
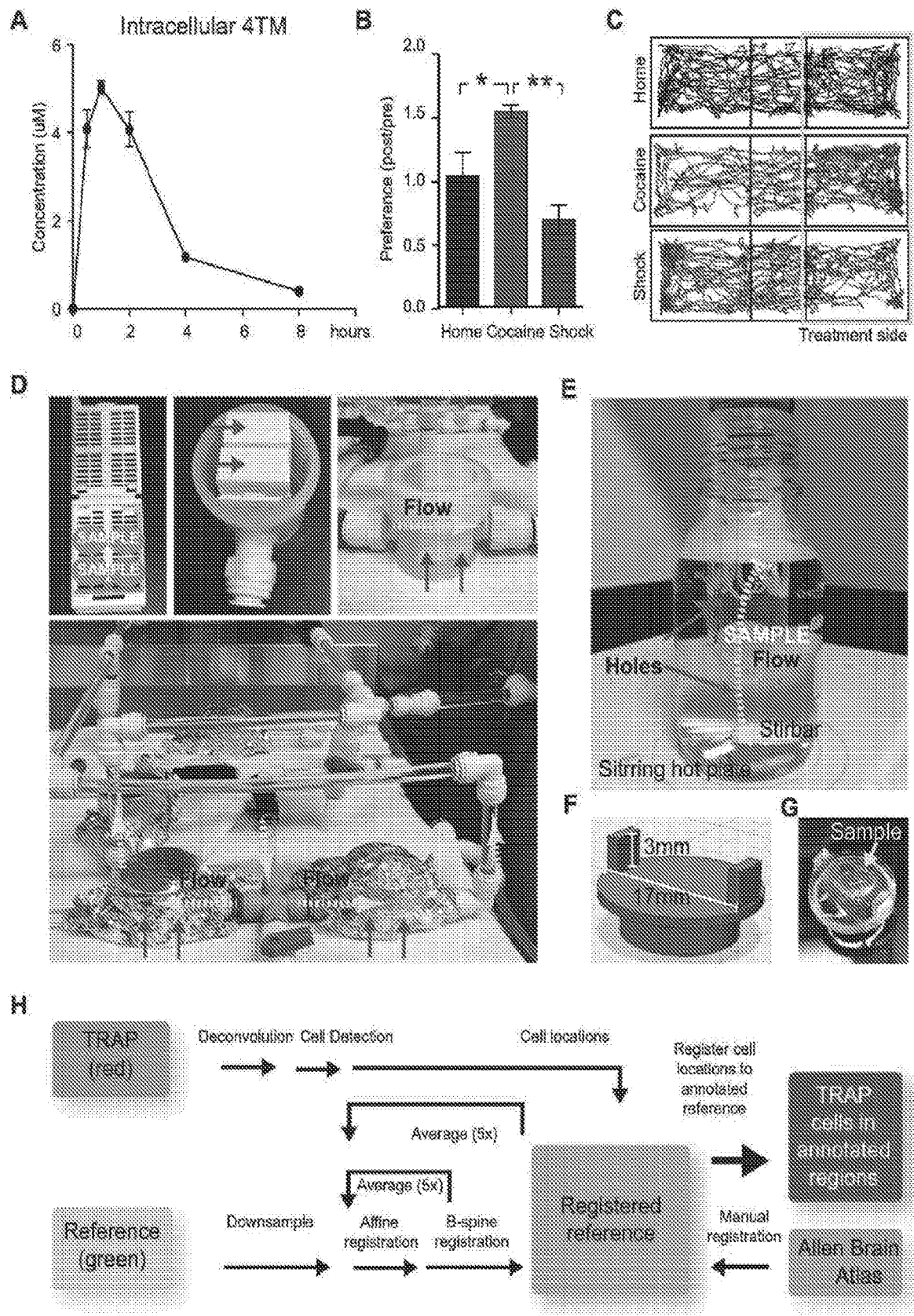
FIG. 1, panels A-H: Figures representing data showing behavioral cohort-scale brainwide activity, images showing the setup of a parallelized flow-assisted clearing device according to one embodiment, and the data processing pipeline according to one embodiment for image registration, cell detection, annotation and quantification.

The term "biological specimen" as used herein refers to any sample of tissue or organ, or any of a variety of sample types obtained from a subject animal or a population of subject animals. The definition encompasses a whole-organ/intact organ sample, such as the brain, or a spinal cord, obtained from a subject animal. A biological specimen of the present disclosure is isolated for imaging analysis according to the methods of the present disclosure.

The term "fixing" or "fixation" as used herein encompasses the process of crosslinking cellular components of a biological specimen to each other, in order to preserve the structure of the specimen and to preserve the specimen from decay. The process of fixation includes contacting the biological specimen with a fixation agent. Various fixation agents are known in the art, and are chosen for use depending on the type of sample, and according to the purpose of fixation.

The term "hydrogel-fixed" or "hydrogel-embedded" as used herein refers to a biological specimen that has been fixed in the presence of hydrogel subunits, methods of which are further described herein. By "hydrogel" is meant a network of polymer chains that are water-insoluble, sometimes found as a colloidal gel in which water is the dispersion medium.

The term "clearing" as used herein refers to the process by which a hydrogel-embedded specimen is made substantially permeable to light. As used herein, the term "CLARITY" refers to a clearing method of preparing a biological specimen for analysis as disclosed in PCT/US2013/031066.

The term "refractive index matching", e.g. as used in the term refractive index matching solution, refers to the process of immersing a subject cleared specimen in a solution to increase the resolution of a microscope when performing image capture. An refractive index matching solution has an index of refraction that closely approximates that of another object (such as a lens of a microscope).

The term "cellular components" generally refers to the unique, highly organized substances of which cells are composed of, e.g., membranes, organelles, proteins, nucleic acids. As used herein, cellular components, e.g., in the removal of cellular components from a biological specimen during the process of clearing, refers to the removal of lipids from the biological specimen.

The term "ionic surfactant" as used herein refers to ionic compounds that lower the surface tension between two substances.

The term "stimulant" as used herein refers to a class of compounds that modulate mental or physical functions, or both. For example, stimulants may include compounds that enhance alertness, wakefulness and locomotion, or compounds that decrease mental and physical function.

The term "image volume" as used herein refers to the volume of interest in a biological specimen that is imaged by, e.g., a light-sheet microscope. The "reference image volume" refers to an image volume obtained by averaging multiple image volumes against an anatomical atlas.

The term "deconvolved" refers to the algorithm-based process used to reverse the effects of convolution on recorded data (e.g., image data).

The term "registration" generally refers to the process of transforming different sets of data into one coordinate system. For example, registration refers to the display of a plurality of images in superposition. "Linear registration" is a type of global image registration and cannot model local geometric differences between images. "Nonlinear", "elastic" or "nonrigid" image registration refers to transformations that are capable of locally warping the target image to align with a reference image.

The term "tractography" as used herein refers to a three-dimensional modeling technique for visually representing fiber-like structures in acquired images. Generally, tractography has been used to visually represent neural tracts using data collected by diffusion tensor imaging. Subject methods of the present disclosure uses tractography to visually represent labeled, e.g., fluorescently labeled fiber-like structures (e.g., ArcTRAP labeled).

The term "streamline" as used herein refers to a line representation obtained by connecting a set of principal fiber-like structure orientations according to the orientation of each. A streamline is generated from a starting seed region and propagated through a field of voxel-wise principal fiber-like structure orientations.

The term "voxel" is based on a contraction of "vox" for volume, and "el" for element, and as used herein, refers to a value on a regular grid in three-dimensional space. In general, the position of a voxel is inferred based upon its position relative to other voxels in an image volume.

As used herein, the term "seed region" or "seed-masked region" refers to a region of origin in which, e.g., a plurality of streamlines are propagated from.

The term "principal fiber-like structure orientation" or "principal fiber orientation" as used herein refers the general direction of a given voxel. The principal fiber-like structure orientation may be generated by processing a plurality of voxels and a predetermined vicinity for each voxel based on image intensity gradients. Details regarding how to generate a principal fiber orientation are further disclosed herein.

The term "image gradient" or "image intensity gradient" as used herein, refers to the directional change in the intensity or color in an image.

As used herein, the term "structure tensor" refers to a matrix derived from the gradient of a function, typically used to represent gradient information.

The term "fractional anisotropy" as used herein, refers to a scalar value between zero and one that describes the degree of anisotropy of a diffusion process, and when used in diffusion imaging, may reflect fiber density, axonal diameter and myelination in white matter of the brain.

DETAILED DESCRIPTION

The present disclosure provides methods of preparing a biological specimen for imaging analysis, comprising fixing and clearing the biological specimen and subsequently analyzing the cleared biological specimen using microscopy. Also included are methods of visualizing a fiber-like structure in a biological specimen obtained from a subject animal. Screening methods for identifying candidate agents that can modify the pattern or dimensions of a fiber-like structure are also provided. Also provides are systems and devices that can be used to carry out methods of the present disclosure.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

The present disclosure provides methods for clearing a biological specimen and analyzing images obtained from the biological specimen. The subject methods include methods for the visualization of a fiber-like structure of a biological specimen obtained from a subject animal. Also provided are screening methods for screening a candidate agent for its ability to modulate the patterning, or size, or diameter of a fiber-like structure. Systems and devices are also provided that carry out visualization methods that are described herein.

Fixing

In some aspects, a biological specimen is fixed in the presence of hydrogel subunits. By "fixing" the specimen it is meant exposing the specimen, i.e., cells of the specimen, to a fixation agent such that the cellular components become crosslinked to one another. By "hydrogel" or "hydrogel network" is meant a network of polymer chains that are water-insoluble, sometimes found as a colloidal gel in which water is the dispersion medium. In other words, hydrogels are a class of polymeric materials that can absorb large amounts of water without dissolving. Hydrogels can contain over 99% water and may comprise natural or synthetic polymers, or a combination thereof. Hydrogels also possess a degree of flexibility very similar to natural tissue, due to their significant water content. A detailed description of suitable hydrogels may be found in published U.S. patent application 20100055733, herein specifically incorporated by reference. By "hydrogel subunits" or "hydrogel precursors" is meant hydrophilic monomers, prepolymers, or polymers that can be crosslinked, or "polymerized", to form a three-dimensional (3D) hydrogel network. Without being bound by any scientific theory, it is believed that this fixation of the biological specimen in the presence of hydrogel subunits crosslinks the components of the specimen to the hydrogel subunits, thereby securing molecular components in place, preserving the tissue architecture and cell morphology.

Any convenient fixation agent, or "fixative," may be used in the fixative/hydrogel composition to fix the specimen in the presence of hydrogel subunits, for example, formaldehyde, paraformaldehyde, glutaraldehyde, acetone, ethanol, methanol, etc. Typically, the fixative will be diluted in a buffer, e.g., saline, phosphate buffer (PB), phosphate buffered saline (PBS), citric acid buffer, potassium phosphate buffer, etc., usually at a concentration of about 1-10%, e.g. 1%, 2%, 3%, 4%, 5%, 6%, 7%, 8%, or 10%, for example, 4% paraformaldehyde/0.1M phosphate buffer; 2% paraformaldehyde/0.2% picric acid/0.1M phosphate buffer; 4% paraformaldehyde/0.2% periodate/1.2% lysine in 0.1M phosphate buffer; 4% paraformaldehyde/0.05% glutaraldehyde in phosphate buffer; etc. The type of fixative used and the duration of exposure to the fixative will depend on the sensitivity of the molecules of interest in the specimen to denaturation by the fixative, and will be known by the ordinarily skilled artisan or may be readily determined using conventional histochemical or immunohistochemical techniques, for example as described in Buchwalow and Böcker. *Immunohistochemistry: Basics and Methods*. Springer-Verlag Berlin Heidelberg 2010.

The fixative/hydrogel composition may comprise any convenient hydrogel subunits, such as, but not limited to, poly(ethylene glycol) and derivatives thereof (e.g. PEG-diacrylate (PEG-DA), PEG-RGD), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose and the like. In some instances, the hydrogel subunits may be modified to add specific properties to the hydrogel; for example, peptide sequences can be incorporated to induce degradation (see, e.g., West and Hubbell, 1999, Macromolecules, 32:241) or to modify cell adhesion (see, e.g. Hern and Hubbell, 1998, J. Biomed. Mater. Res., 39:266). Agents such as hydrophilic nanoparticles, e.g., poly-lactic acid (PLA), poly-glycolic acid (PLG), poly(lactic-co-glycolic acid) (PLGA), polystyrene, poly(dimethylsiloxane) (PDMS), etc. may be used to improve the permeability of the hydrogel while maintaining patternability (see, e.g., U.S. patent application Ser. No. 13/065,030; Lee W. et al. 2010 Proc. Natl. Acad. Sci. 107, 20709-20714). Materials such as block copolymers of PEG, degradable PEO, poly(lactic acid) (PLA), and other similar materials can be used to add specific properties to the hydrogels (see, e.g., Huh and Bae, 1999, Polymer, 40:6147). Crosslinkers (e.g. bis-acrylamide, diazirine, etc.) and initiatiors (e.g. azobisisobutyronitrile (AIBN), riboflavin, L-arginine, etc.) may be included to promote covalent bonding between interacting macromolecules in later polymerization steps.

Typically, the concentration and molecular weight of the hydrogel subunit(s) and modifying agents will depend on the selected polymer and the desired characteristics, e.g., pore size, swelling properties, conductivity, elasticity/stiffness (Young's modulus), biodegradability index, etc., of the hydrogel network into which they will be polymerized. For example, it may be desirable for the hydrogel to comprise pores of sufficient size to allow the passage of macromolecules, e.g., proteins, nucleic acids, or small molecules as described in greater detail below, into the specimen. The ordinarily skilled artisan will be aware that pore size generally decreases with increasing concentration of hydrogel subunits and generally increases with an increasing ratio of hydrogel subunits to crosslinker, and will prepare a fixative/hydrogel composition that comprises a concentration of hydrogel subunits that allows the passage of such macromolecules. As another example, it may be desirable for the hydrogel to have a particular stiffness, e.g., to provide stability in handling the embedded specimen, e.g., a Young's Modulus of about 2-70 kN/m$^2$, for example, about 2 kN/m$^2$, about 4 kN/m$^2$, about 7 kN/m$^2$, about 10 kN/m$^2$, about 15 kN/m$^2$, about 20 kN/m$^2$, about 40 kN/m$^2$, but typically not more than about 70 kN/m$^2$. The ordinarily skilled artisan will be aware that the elasticity of a hydrogel network may be influenced by a variety of factors, including the branching of the polymer, the concentration of hydrogel subunits, and the degree of cross-linking, and will prepare a fixative/hydrogel composition that comprises a concentration of hydrogel subunits to provide such desired elasticity. Thus, for example, the fixative/hydrogel composition may comprise an acrylamide monomer at a concentration of from about 1% w/v to about 20% w/v, e.g., about 2% to about 15%, about 3% to about 10%, about 4% to about 8%, and a concentration of bis-acrylamide crosslinker in the range of about 0.01% to about 0.15%, e.g., 0.01%, 0.02%, 0.025%, 0.03%, 0.04%, 0.05%, 0.06%, 0.075%, 0.08%, 0.09%, 0.1% or 0.125%; or, for example, the fixative/hydrogel composition may comprise PEG prepolymers having a molecular weight ranging from at least about 2.5K to about 50K, e.g., 2.5K or more, 3.5K or more, 5K or more, 7.5K or more, 10K or more, 15K or more, 20K or more, but typically not more than about 50K, at a concentration in a range from about 1% w/w to about 50% w/w, e.g., 1% or more, 5% or more, 7.5% or more, 10% or more, 15% or more, 20% or more, 30% or more, 40% or more, and usually not more than about 50%. Concentrations of hydrogel subunits and modifiers that provide desired hydrogel characteristics may be readily determined by methods in the art or as described in the working examples below.

The fixative/hydrogel solution may be delivered to the specimen by any convenient method, e.g., perfusion, injection, instillation, absorption, application, immersion/submersion, etc. In certain aspects, the subject method delivers the hydrogel solution to the specimen using a non-perfusion-based method. The specimen will typically be fixed in the presence of the hydrogel for 15 minutes or more, for example, for 30 minutes or more, 1 hour or more, 2 hours or more, 4 hours or more, 6 hours or more, 12 hours or more, in some instances, for 16 hours or more, 20 hours or more, 24 hours or more, or 48 hours or more.

Following fixation of the specimen, the hydrogel subunits are polymerized, i.e., covalently or physically crosslinked, to form a hydrogel network. Polymerization may be induced by any method including, but not limited to, thermal crosslinking, chemical crosslinking, physical crosslinking, ionic crosslinking, photo-crosslinking, irradiative crosslinking (e.g., x-ray, electron beam), and the like, and may be selected based on the type of hydrogel used and knowledge in the art. For example, mixing of an un-polymerized or partially polymerized resin with specific crosslinking chemicals results in a chemical reaction that forms cross-links. As another example, polymerization can be induced by the addition of a non-nitrile azo thermal initiator, such as VA-044, which is inert at lower temperatures, but generates free radicals in solution at higher temperatures. The free radicals that are generated initiate polymerization of the acrylamide monomers to form a crosslinked hydrogel network. Concentrations of crosslinking agents and thermal initiators may be readily determined by methods in the art or as described in the working examples below. Crosslinking can be induced in materials that are normally thermoplastic through exposure to a radiation source, such as electron beam exposure, gamma-radiation, or UV light; for example, electron beam processing is used to polymerize the C type of crosslinked polyethylene. Other types of crosslinked polyethylene are made by addition of peroxide during extruding (type A) or by addition of a cross-linking agent (e.g. vinylsilane) and a catalyst during extruding and then performing a post-extrusion curing. Many polymers undergo oxidative cross-linking, typically when exposed to atmospheric oxygen. In some cases the reaction is more rapid than desired and thus polymerization reactions may involve the use of an antioxidant to slow the formation of oxidative cross-links. In other cases, e.g., when more rapid formation of cross-links by oxidation is desirable, an oxidizer such as hydrogen peroxide may be used to speed up the process. The length of time for polymerization will depend on the type of hydrogel subunits used and the chosen polymerization method, but will typically be about 15 minutes to about 48 hours, for example, 15 minutes or more, 1 hour or more, 2 hours or more, 3 hours or more, 4 hours or more, 6 hours or more, 12 hours or more, 16 hours or more, 24 hours or more, or in some instances, 48 hours. The optimal time and combination of reagents will be known to the ordinarily skilled artisan or may be determined empirically or from any number of publicly available resources (e.g., on the world wide web at piercenet.com; see also, Macroporous Polymers: Production Properties and Biotechnological/Biomedical Applications. Edited by Bo Mattiasson, Ashok Kumar, and Igor Yu. Galeaev. CRC Press 2010; and Crosslinking Reagents Technical Handbook, Pierce Biotechnology, Inc., 2006).

Clearing

Once polymerized, the hydrogel-embedded (i.e., hydrogel-hybridized) specimen may be cleared. By "clearing" a specimen it is meant that the specimen is made substantially permeable to light, i.e., transparent. In other words, about 70% or more of the visual (i.e., white) light, ultraviolet light or infrared light that is used to illuminate the specimen will to pass through the specimen and illuminate only selected cellular components therein, e.g., 75% or more of the light, 80% or more of the light, 85% or more of the light, in some instances, 90% or more of the light, 95% or more of the light, 98% or more of the light, e.g. 100% of the light will pass through the specimen. This change in the optical properties of the specimen provides for the visualization of cellular and subcellular structures internal to the tissue.

Any treatment that forces cellular components, e.g., lipids, from the specimen, that draws cellular components, e.g., lipids, from a specimen, or that causes cellular components, e.g., lipids, to break down, i.e., dissolve, within a specimen may be used to clear the specimen, including, without limitation, exposure to organic solvents such as xylenes, ethanol or methanol, exposure to detergents such as saponin, Triton X-100 and Tween-20, exposure to ionic surfactants, e.g., sodium dodecyl sulfate (SDS), electrophoresis, hydrodynamic pressure, ultrasonic vibration, solute contrasts, microwave radiation, vascular circulation, and the like. In some instances, clearing is performed using a solvent that does not quench fluorescent proteins. Examples of organic solvents that are known to quench fluorescent proteins include tetrahydrofuran, hexane, benzylalcohol/benzylbenzoate (BABB), and dibenzyl ether. Accordingly, in order to preserve the fluorescence of various proteins, in some embodiments clearing is conducted using solvents other than those listed above, e.g., is conducted using non-organic solvents.

In some instances, clearing is conducted using an ionic surfactant, e.g., SDS, in order to expedite the clearing process by actively transporting charged ionic micelles out of the specimen that is being cleared. Clearing may be performed in any convenient buffer that is compatible with the selected clearance method, e.g., saline, phosphate buffer, phosphate buffered saline (PBS), sodium borate buffer, boric acid buffer, citric acid buffer, etc., as known in the art, and will typically take about 1-10 days per centimeter thickness of specimen, i.e., usually about 1 day, in some instances 2 days, sometimes 5 days, and typically no more than 10 days per cubic centimeter. Optimal time may be readily determined by visual inspection of the specimen for clarity.

After clearing, a sample will generally be substantially free of lipids. By "substantially free of lipids" is meant that the original amount of lipids present in the sample before clearing has been reduced by approximately 70% or more, such as by 75% or more, such as by 80% or more, such as by 85% or more, such as by 90% or more, such as by 95% or more, such as by 99% or more, such as by 100%.

Post-Clearing

In some instances, no further manipulation of the specimen will be necessary for microscopic analysis. For example, the specimen may comprise biomolecules that can be directly visualized by microscopy. By "biomolecules" it is generally meant proteins, lipids, steroids, nucleic acids, etc. within a tissue or cell. One example of this would be if the organism that was the source of the specimen expressed a protein that possesses the ability to fluoresce, i.e. a "fluorescent protein", or "FP". By "fluoresce" is meant to absorb energy at one wavelength and emit it at another wavelength. For example, a green fluorescent protein (GFP) refers to a polypeptide that has a peak in the emission spectrum at 510 nm or about 510 nm. A variety of FPs that emit at various wavelengths are known in the art. FPs of interest include, but are not limited to, a green fluorescent protein (GFP), yellow fluorescent protein (YFP), orange fluorescent protein (OFP), cyan fluorescent protein (CFP), blue fluorescent protein (BFP), red fluorescent protein (RFP), far-red fluorescent protein, or near-infrared fluorescent protein. As used herein, *Aequorea* GFP refers to GFPs from the genus *Aequorea* and to mutants or variants thereof. Such variants and GFPs from other species, such as Anthozoa reef coral, *Anemonia* sea anemone, *Renilla* sea pansy, *Galaxea* coral, *Acropora* brown coral, *Trachyphyllia* and *Pectimidae* stony coral and other species are well known and are available and known to those of skill in the art. Exemplary GFP variants include, but are not limited to BFP, CFP, YFP and OFP. Examples of florescent proteins and their variants include GFP proteins, such as Emerald (Invitrogen, Carlsbad, Calif.), EGFP (Clontech, Palo Alto, Calif.), Azami-Green (MBL International, Woburn, Mass.), Kaede (MBL International, Woburn, Mass.), ZsGreenl (Clontech, Palo Alto, Calif.) and CopGFP (Evrogen/Axxora, LLC, San Diego, Calif.); CFP proteins, such as Cerulean (Rizzo, Nat Biotechnol. 22(4):445-9 (2004)), mCFP (Wang et al., PNAS USA. 101(48):16745-9 (2004)), AmCyanl (Clontech, Palo Alto, Calif.), MiCy (MBL International, Woburn, Mass.), and CyPet (Nguyen and Daugherty, Nat Biotechnol. 23(3): 355-60 (2005)); BFP proteins such as EBFP (Clontech, Palo Alto, Calif.); YFP proteins such as EYFP (Clontech, Palo Alto, Calif.), YPet (Nguyen and Daugherty, Nat Biotechnol. 23(3):355-60 (2005)), Venus (Nagai et al., Nat. Biotechnol. 20(1):87-90 (2002)), ZsYellow (Clontech, Palo Alto, Calif.), and mCitrine (Wang et al., PNAS USA. 101(48):16745-9 (2004)); OFP proteins such as cOFP (Strategene, La Jolla, Calif.), mKO (MBL International, Woburn, Mass.), and mOrange; and others (Shaner N C, Steinbach P A, and Tsien R Y., Nat Methods. 2(12):905-9 (2005)). Another class of fluorescent proteins is the red fluorescent protein Discosoma RFP (DsRed) that has been isolated from the corallimorph Discosoma (Matz et al., Nature Biotechnology 17: 969-973 (1999)), and red or far-red fluorescent proteins from any other species, such as *Heteractis* reef coral and *Actinia* or *Entacmaea* sea anemone, as well as variants thereof RFPs include, for example, Discosoma variants, such as monomeric red fluorescent protein 1 (mRFP1), mCherry, tdTomato, mStrawberry, mTangerine (Wang et al., PNAS USA. 101(48):16745-9 (2004)), DsRed2 (Clontech, Palo Alto, Calif.), and DsRed-T1 (Bevis and Glick, Nat. Biotechnol., 20: 83-87 (2002)), Anthomedusa J-Red (Evrogen) and *Anemonia* AsRed2 (Clontech, Palo Alto, Calif.). Far-red fluorescent proteins include, for example, *Actinia* AQ143 (Shkrob et al., Biochem J. 392(Pt 3):649-54 (2005)), *Entacmaea* eqFP611 (Wiedenmann et al. Proc Natl Acad Sci USA. 99(18):11646-51 (2002)), Discosoma variants such as mPlum and mRasberry (Wang et al., PNAS USA. 101(48): 16745-9 (2004)), and *Heteractis* HcRed1 and t-HcRed (Clontech, Palo Alto, Calif.).

Additionally or alternatively, it may be desirable to contact the cells and intracellular structures of the specimen with one or more macromolecules prior to microscopic analysis. For example, macromolecules may be provided that promote the visualization of particular cellular biomolecules, e.g., proteins, lipids, steroids, nucleic acids, etc. and sub-cellular structures. In some embodiments, the macromolecules are diagnostic. In some embodiments, the macromolecules are prognostic. In some embodiments, the macromolecules are predictive of responsiveness to a therapy. In some embodiments, the macromolecules are candidate agents in a screen, e.g., a screen for agents that will aid in the diagnosis and/or prognosis of disease, in the treatment of a disease, and the like.

For example, specimens may be contacted with nucleic acid stains like DAPI and Hoechst, which bind the minor groove of DNA, thus labeling the nuclei of cells. Drugs or toxins that bind specific cellular structures and have been derivatized with a fluorescent reporter may be employed, e.g., fluorescently labelled-phalloidin, which is used to stain actin fibers in mammalian cells. There are many fluorescent reported molecules, called fluorophores or fluorochromes such as fluorescein, Alexa Fluors or DyLight 488, which can be chemically linked to molecules which bind the target biomolecules of interest within the sample.

As another example, the specimen may be contacted with one or more polypeptides, e.g. antibodies, labeled peptides, and the like, that are specific for and will bind to particular cellular biomolecules for either direct or indirect labeling by color or immunofluorescence. By immunofluorescence it is meant a technique that uses the highly specific binding of an antibody to its antigen or binding partner in order to label specific proteins or other molecules within the cell. A sample is treated with a primary antibody specific for the biomolecule of interest. A fluorophore can be directly conjugated to the primary antibody or peptide. Alternatively a secondary antibody, conjugated to a detection moiety or fluorophore, which binds specifically to the first antibody can be used. See, for example, Buchwalow and Bocker. Immunohistochemistry: Basics and Methods, Springer-Verlag, Berlin Heidelberg 2010, and Hayat, M. A. Microscopy, Immunohistochemistry, and Antigen Retrieval Methods for Light and Electron Microscopy. Kluwar Academic Publishers, New York 2002, for examples of protocols that may be followed. Peptides that are specific for a target cellular biomolecule and that are conjugated to a fluorophor or other detection moiety may also be employed.

Another example of a class of agents that may be provided as macromolecules is nucleic acids. For example, a specimen may be contacted with an antisense RNA that is complementary to and specifically hybridizes to a transcript of a gene of interest, e.g., to study gene expression in cells of the specimen. As another example, a specimen may be contacted with a DNA that is complementary to and specifically hybridizes to genomic material of interest, e.g., to study genetic mutations, e.g., loss of heterozygosity, gene duplication, chromosomal inversions, and the like. The hybridizing RNA or DNA is conjugated to detection moieties, i.e. agents that may be either directly or indirectly visualized microscopically. Examples of in situ hybridization techniques may be found at, for example, Harris and Wilkinson. In situ hybridization: Application to developmental biology and medicine, Cambridge University Press 1990; and Fluorescence In Situ Hybridization (FISH) Application Guide. Liehr, T, ed., Springer-Verlag, Berlin Heidelberg 1990.

As another example, the specimen may be contacted with small molecules. For example, if the specimen comprises β-galactosidase or alkaline phosphatase, it may be desirable to visualize cells and regions of the tissue expressing these proteins. Towards this end, a specimen may be contacted with substrates for β-galactosidase (e.g. X-gal, 4-Trifluoromethylumbelliferyl-β-D-galactopyranoside (TFMU-Gal), Resoruf in β-D-galactopyranoside (Res-gal), 4-Methylumbelliferyl β-D-galactopyranoside (MUG), di-β-D-galactopyranoside (FDG), Carboxyumbelliferyl β-D-galactopyranoside (CUG)) or for alkaline phosphatase (e.g. nitro-blue tetrazolium (NBT)/5-bromo-4-chloro-3'-indolyphosphate (BCIP)) and other reagents that allow for visualization of β-galactosidase or alkaline phosphatase activity. As another example, it may be desirous to visualize the dendritic arbors and spins of neurons in, e.g., a CNS specimen. To do so, the specimen may be exposed to chemicals used in Golgi-Cox impregnation, e.g., 3% potassium bichromate followed by a 2% silver nitrate solution.

In some instances, the biomolecules that are targeted by the provided macromolecules are endogenous to the cell. In other instances, the macromolecules may be provided to the specimen to target/visualize biomolecules that were ectopically provided to the cells of the specimen, e.g. agents that were introduced to the specimen in vivo or ex vivo to label certain cell populations or subcellular structures. For example, stereotactic surgery is often used in the field of neuroscience to provide biomolecules such as proteins, viruses, chemicals to neural tissue that label, or "trace", the projections and/or the connectivity of subsets of neurons in vivo or ex vivo. In this technique, a needle comprising a labeling macromolecule is lowered into CNS tissue at a precise location and the labeling molecule is released into the tissue. The molecule will fill the neurons in the vicinity of the injection site and, depending on the type of macromolecule delivered, may be transported across synapses to label their efferent targets ("anterograde tracing") and/or across dendrites to label the afferent neurons from which they are receiving signals ("retrograde tracing"). Examples of agents that may be used to label neurons stereotactically are well known in the art, including, for example, nucleic acids that encode fluorescent proteins; viral tracers, e.g. Herpes simplex virus type1 (HSV) and the Rhabdoviruses; wheat-germ agglutinin (WGA); Phaseolus vulgaris leucoagglutinin (PHA-L); horseradish peroxidase-conjugated lectins; biotinylated dextran amines (BDA); cholera toxin B; NEUROBIOTIN Tracer® (Vector labs). Specimens labeled in this way may be contacted with macromolecules, e.g. polypeptides or chemicals, that promote the visualization of these ectopically provided labels.

In some instances, the macromolecules that are used to visualize the cellular biomolecules or subcellular structures are passively transported into the specimen. In other words, the macromolecules diffuse into the specimen. In other instances, the macromolecules are actively transported into the specimen, e.g. by electroporation, hydrodynamic pressure, ultrasonic vibration, solute contrasts, microwave radiation, vascular circulation, or the like. In some embodiments, the specimen is contacted with the macromolecules after the specimen has been cleared. In other embodiments, the hydrogel-embedded specimen may be contacted with macromolecules prior to clearing the specimen. In such embodiments, contact with the macromolecules may be facilitated by permeabilizing the specimen, that is, changing the properties of the specimen to improve the permeability of the specimen to macromolecules. By a "permeabilized" specimen it is meant that about 50% or more of the macromolecules applied to the specimen will penetrate to the deepest regions of the specimen, e.g. 60% or more of the macromolecules, 70% or more of the macromolecules, or 80% or more of the macromolecules, in some instances 85% or more of the macromolecules, 90% or more of the macromolecules, or 95% or more of the macromolecules, for example 98% or more of the macromolecules, e.g. 100% of the macromolecules will pass through the specimen. Permeabilization of the specimen, and of the cells therein, may be achieved by any of the protocols discussed above for the removal of cellular components, e.g. lipids, from the specimen or as known in the art for permeabilizing cells.

In some instances, a technique called Targeted Recombination in Active Populations (TRAP) may be employed to identify a certain active population of cells within a specimen. In some aspects, TRAP is used to identify a neuronal population within a specimen that is activated by experiences. In some cases, an activated neuronal population may be identified by genetically engineering a subject animal to obtain permanent or temporary genetic access to the activated neuronal population. TRAP utilizes two genetic components: a transgene that takes advantage of immediate early gene (IEG) regulatory elements to express a drug-dependent recombinase (e.g., tamoxifen-dependent Cre recombinase CreER$^{T2}$), in an activity-dependent manner, and a transgene or virus that expresses an effector protein in a recombination-dependent manner. IEGs are genes which are activated transiently and rapidly in response to a wide variety of defined stimuli, and represent a standing response mechanism that is activated at the transcription level in the first round of response to the defined stimuli. TRAP may utilize any endogenous IEG loci of the subject animal, including, but not limited to: Fos, Arc and jun, to express a drug-dependent recombinase (e.g., tamoxifen-dependent Cre recombinase CreER$^{T2}$). TRAP can selectively provide access to neurons activated by, but not limited to, specific somatosensory, visual, and auditory stimuli, and by experience in a novel environment. See, e.g., Guenthner et al., Neuron (2013) 78(5):773-784.

Suitable Specimens

Tissue specimens suitable for use with the methods and systems described herein generally include any type of tissue specimens collected from living or dead subjects, such as, e.g., biopsy specimens and autopsy specimens. Tissue specimens may be collected and processed using the methods and systems described herein and subjected to microscopic analysis immediately following processing, or may be preserved and subjected to microscopic analysis at a future time, e.g., after storage for an extended period of time. In some embodiments, the methods described herein may be used to preserve tissue specimens in a stable, accessible and fully intact form for future analysis. For example, tissue specimens, such as, e.g., human brain tissue specimens, skin specimens, specimens containing vasculature, human heart tissue specimens, may be processed as described above and cleared to remove a plurality of cellular components, such as, e.g., lipids, and then stored for future analysis. In some embodiments, the methods and systems described herein may be used to analyze a previously-preserved or stored tissue specimen. For example, in some embodiments a previously-preserved tissue specimen that has not been subjected to the CLARITY process may be processed and analyzed as described herein.

Microscopic Analysis

To microscopically visualize specimens prepared by the subject methods, in some embodiments the specimen is embedded in a mounting medium. Mounting medium is typically selected based on its suitability for the reagents used to visualize the cellular biomolecules, the refractive index of the specimen, and the microscopic analysis to be performed. For example, for phase-contrast work, the refractive index of the mounting medium should be different from the refractive index of the specimen, whereas for bright-field work the refractive indexes should be similar. As another example, for epifluorescence work, a mounting medium should be selected that reduces fading, photobleaching or quenching during microscopy or storage. In certain embodiments, a mounting medium or mounting solution may be selected to enhance or increase the optical clarity of the cleared tissue specimen. Nonlimiting examples of suitable mounting media that may be used include glycerol, CC/Mount™, Fluoromount™ Fluoroshield™, ImmunHistoMount™, Vectashield™, Permount™, Acrytol™, CureMount™, FocusClear™, RapidClear™, or equivalents thereof.

In some instances, the hydrogel-embedded specimen is permanently mounted. In other words, once mounted in mounting medium, the hydrogel-embedded specimen cannot be removed for further manipulation. In other instances, the specimen is temporarily, or reversibly, mounted. In other words, the hydrogel-embedded specimen may be removed from the mounting medium and re-stained after microscopy to visualize alternative/additional biomolecules or subcellular structures. In such instances, macromolecules that were previously added to the specimen, e.g. to visualize certain biomolecules, may be removed after microscopic analysis by, e.g., exposure to organic solvents such as xylenes, ethanol or methanol, exposure to detergents such as sodium dodecyl sulfate (SDS), saponin, Triton X-100 and Tween-20, electrophoresis, hydrodynamic pressure, ultrasonic vibration, solute contrasts, microwave radiation, vascular circulation, and the like. The hydrogel-embedded specimen is then contacted with different macromolecules specific for other biomolecules or subcellular structures. As such, iterative staining may be performed on the same specimen.

Specimens prepared using the subject methods may be analyzed by any of a number of different types of microscopy, for example, optical microscopy (e.g. bright field, oblique illumination, dark field, phase contrast, differential interference contrast, interference reflection, epifluorescence, confocal, etc., microscopy), laser microscopy, electron microscopy, and scanning probe microscopy.

Bright field microscopy is the simplest of all the optical microscopy techniques. Sample illumination is via transmitted white light, i.e. illuminated from below and observed from above. Limitations include low contrast of most biological samples and low apparent resolution due to the blur of out of focus material. The simplicity of the technique and the minimal sample preparation required are significant advantages.

In oblique illumination microscopy, the specimen is illuminated from the side. This gives the image a 3-dimensional appearance and can highlight otherwise invisible features. A more recent technique based on this method is Hoffmann's modulation contrast, a system found on inverted microscopes for use in cell culture. Though oblique illumination suffers from the same limitations as bright field microscopy (low contrast of many biological samples; low apparent resolution due to out of focus objects), it may highlight otherwise invisible structures.

Dark field microscopy is a technique for improving the contrast of unstained, transparent specimens. Dark field illumination uses a carefully aligned light source to minimize the quantity of directly-transmitted (unscattered) light entering the image plane, collecting only the light scattered by the sample. Dark field can dramatically improve image contrast (especially of transparent objects) while requiring little equipment setup or sample preparation. However, the technique suffers from low light intensity in final image of many biological samples, and continues to be affected by low apparent resolution.

Phase contrast is an optical microscopy illumination technique that converts phase shifts in light passing through a transparent specimen to brightness changes in the image. In other words, phase contrast shows differences in refractive index as difference in contrast. The phase shifts themselves are invisible to the human eye, but become visible when they are shown as brightness changes.

In differential interference contrast (DIC) microscopy, differences in optical density will show up as differences in relief. The system consists of a special prism (Nomarski prism, Wollaston prism) in the condenser that splits light in an ordinary and an extraordinary beam. The spatial difference between the two beams is minimal (less than the maximum resolution of the objective). After passage through the specimen, the beams are reunited by a similar prism in the objective. In a homogeneous specimen, there is no difference between the two beams, and no contrast is being generated. However, near a refractive boundary (e.g. a nucleus within the cytoplasm), the difference between the ordinary and the extraordinary beam will generate a relief in the image. Differential interference contrast requires a polarized light source to function; two polarizing filters have to be fitted in the light path, one below the condenser (the polarizer), and the other above the objective (the analyzer).

Another microscopic technique using interference is interference reflection microscopy (also known as reflected interference contrast, or RIC). It is used to examine the adhesion of cells to a glass surface, using polarized light of a narrow range of wavelengths to be reflected whenever there is an interface between two substances with different refractive indices. Whenever a cell is attached to the glass surface, reflected light from the glass and that from the attached cell will interfere. If there is no cell attached to the glass, there will be no interference.

A fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" refers to any microscope that uses fluorescence to generate an image, whether it is a more simple set up like an epifluorescence microscope, or a more complicated design such as a confocal microscope, which uses optical sectioning to get better resolution of the fluorescent image.

Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples.

In single plane illumination microscopy (SPIM), also known as light sheet microscopy, only the fluorophores in the focal plane of the detection objective lens are illuminated. The light sheet is a beam that is collimated in one and focused in the other direction. Since no fluorophores are excited outside the detectors' focal plane, the method also provides intrinsic optical sectioning. Moreover, when compared to conventional microscopy, light sheet methods exhibit reduced photobleaching and lower phototoxicity, and often enable far more scans per specimen. By rotating the specimen, the technique can image virtually any plane with multiple views obtained from different angles. In some cases, a specimen cleared by methods of the present disclosure may be imaged with high resolution by illuminating the cleared specimen with two light sheets from a first side and a second side to produce an image volume.

Super-resolution microscopy is a form of light microscopy. Due to the diffraction of light, the resolution of conventional light microscopy is limited as stated by Ernst Abbe in 1873. A good approximation of the resolution attainable is the FWHM (full width at half-maximum) of the point spread function, and a precise widefield microscope with high numerical aperture and visible light usually reaches a resolution of ~250 nm. Super-resolution techniques allow the capture of images with a higher resolution than the diffraction limit. They fall into two broad categories, "true" super-resolution techniques, which capture information contained in evanescent waves, and "functional" super-resolution techniques, which use experimental techniques and known limitations on the matter being imaged to reconstruct a super-resolution image.

Laser microscopy uses laser illumination sources in various forms of microscopy. For instance, laser microscopy focused on biological applications uses ultrashort pulse lasers, or femtosecond lasers, in a number of techniques including nonlinear microscopy, saturation microscopy, and multiphoton fluorescence microscopy such as two-photon excitation microscopy (a fluorescence imaging technique that allows imaging of living tissue up to a very high depth, e.g. one millimeter)

In electron microscopy (EM), a beam of electrons is used to illuminate a specimen and produce a magnified image. An electron microscope has greater resolving power than a light-powered optical microscope because electrons have wavelengths about 100,000 times shorter than visible light (photons). They can achieve better than 50 pm resolution and magnifications of up to about 10,000,000× whereas ordinary, non-confocal light microscopes are limited by diffraction to about 200 nm resolution and useful magnifications below 2000×. The electron microscope uses electrostatic and electromagnetic "lenses" to control the electron beam and focus it to form an image. These lenses are analogous to but different from the glass lenses of an optical microscope that forms a magnified image by focusing light on or through the specimen. Electron microscopes are used to observe a wide range of biological and inorganic specimens including microorganisms, cells, large molecules, biopsy samples, metals, and crystals. Industrially, the electron microscope is often used for quality control and failure analysis. Examples of electron microscopy include Transmission electron microscopy (TEM), Scanning electron microscopy (SEM), reflection electron microscopy (REM), Scanning transmission electron microscopy (STEM) and low-voltage electron microscopy (LVEM).

Scanning probe microscopy (SPM) is a branch of microscopy that forms images of surfaces using a physical probe that scans the specimen. An image of the surface is obtained by mechanically moving the probe in a raster scan of the specimen, line by line, and recording the probe-surface interaction as a function of position. Examples of SPM include atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM).

Examples of imaging and analysis devices suitable for use in carrying out the subject methods also include a CLARITY optimized light-sheet microscope (COLM), which image large intact tissue samples. Such methods involve placing a sample in the sample chamber of an optically homogenous sample manipulation component, performing a calibration procedure to align a light sheet and a detection focal plane of a microscope device at a plurality of locations within the sample to acquire an alignment parameter for each location, performing an imaging procedure to collect an image from each of the plurality of locations within the sample, and constructing a three-dimensional image of the sample using the image from each location. Additional description may be found in, e.g., U.S. Patent Application No. 2017/0068086, the disclosure of which is incorporated herein by reference.

Tractography

Various tractography algorithms can be applied to acquired image data (e.g., image volumes from light-sheet microscopic analysis) of a cleared biological specimen to determine tracts (e.g., axon tracts) of a fiber-like structure. As discussed further herein, various tractography algorithms can require manual input, such as determination of a region of interest or a seed region/point, or can include automatic input. Further, multiple algorithms (e.g., linear, fast marching, energy, minimization, or other generally known algorithms) and multiple seed regions can be used to define tracts relative to the image data of the cleared biological specimen.

Tractography methods and algorithms akin to what is used for diffusion magnetic resonance imaging, including those discussed further herein, can be used to identify tracts within a cleared biological specimen. As is understood by one skilled in the art, fluorescence imaging data (e.g., CLARITY images) can be used to illustrate the various portions of the cleared biological specimen based upon a plurality of streamlines from a seed region of a voxel of the image data acquired by the imaging system. See The Visualization Handbook, "Diffusion Tensor MRI Visualization," pgs. 317-330 (2004) which is incorporated herein by reference.

In general, tractography methods are performed using data from imaging analysis. For example, tractography may be performed using fluorescence imaging data (e.g., CLARITY images) collected from light-sheet microscopic analysis. For example, the tractography algorithm as used by Mori et al., Annals of Neurology (1999) 45:265-269, the disclosure of which is herein incorporated by reference in its entirety, may be applied to imaging data to propagate streamlines from a seed region through a vector field of voxel-wise fiber orientations. See Behrens, et al., NeurolImage (2007) 34(1): 144-155 for detailed methods of tractography algorithms.

A CLARITY image can be processed using an appropriate software program known in the art. For example, in certain embodiments, the image is processed using custom software. All custom software, including scripts used in subject methods of the instant disclosure are available at "http" followed by "://capture-clarity." followed by "org/" (password for review: dlab2016). Preprocessing of a CLARITY image may consist of correction using affine registration and extraction to exclude non-relevant tissue. Various processing techniques are known to those of skill in the art and can be modified for specific enhancements and hardware platforms applicable to the presently disclosed subject matter.

Starting from voxels within a specified seed masked region, tracts can be tracked using streamlines that propagate through a vector field of voxel-wise principal fiber orientations. Streamline propagation can be achieved using algorithms or through manual input.

"Seeding" refers to a technique that computationally registers the images of cleared biological specimens acquired by microscopic analysis, and then selects fibers from a "seeded" region which can be manually or automatically defined. The seed region can be defined both structurally (e.g., an anatomical landmark) and functionally (e.g., active region due to stimulation).

Since tractography results can differ depending on the size and location of the seed region (origin of the fiber tract) masks used, anatomical masks can be created in normal space using an atlas (e.g., Allen brain atlas), which can be included in software packages. A mask is the area identified as the destination or origin of the identified fiber-like tracts.

Because there is a possibility that fiber-like structures from one anatomical region can differ stimulated and non-stimulation, tractography analysis can be conducted to identify all tracts originating from the anatomical region before specifying masks to isolate specific tracts. Appropriate masks can be specified to isolate individual fiber-like structures or tracts. Masks can be chosen based on known anatomy, and can be confirmed by visual inspection to assure accuracy, or to assure that masked regions overlap with active structures (e.g., due to stimulation) as expected. All steps can be varied as needed by those of skill in the art depending upon specific goals, formats, platforms, software versions, scanner vendors, and other site-specific factors.

In some aspects, a tractography methodology for visualizing a fiber-like structure of the present disclosure uses a tractography algorithm that propagates streamlines from a seed region through a vector field of voxel-wise principal fiber orientations. In some cases, the propagated streamlines terminate if a streamline makes a sharp turn, such as, e.g., of a turn angle larger than a prescribed threshold $\alpha_{thresh}$ value, or if a streamline ventures outside of a masked region. The criteria for streamline termination may be set by the user and can include a "loop-check" to make sure streamlines do not circle back on themselves. A streamline may also be set to terminate once it reaches a specific region of interest or when fractional anisotropy drops below a certain threshold. In some aspects, a vector field of voxel-wise principal fiber orientations may be generated by first defining a plurality of voxels within a representation of the fiber-like structure, and then processing each of the plurality of voxels to estimate a plurality of principal fiber-like structure orientations. In some cases, processing each of the plurality of voxels may include: identifying a plurality of image intensity gradients within a predetermined vicinity of the voxel, determining a structure tensor using the plurality of image intensity gradients; and estimating a principal fiber-like structure orientation from the structure tensor.

In some aspects, a structure tensor may be defined as:

$S_w(p) = \iiint_{R^3} w(r) S_0(p-r) dr$ where p and r represent spatial locations, w is a Gaussian weighing function with standard deviation $\sigma_g$, $S_0$ is a symmetric second-moment matrix derived from image intensity gradients:

$$S_0(p) = \begin{pmatrix} (I_x(p))^2 & I_x(p)I_y(p) & I_x(p)I_z(p) \\ I_y(p)I_x(p) & (I_y(p))^2 & I_y(p)I_z(p) \\ I_z(p)I_x(p) & I_z(p)I_y(p) & (I_z(p))^2 \end{pmatrix}$$

where $I_x$, $I_y$, and $I_z$, are the gradients of image intensity I along each of the x, y and z axes, computed by convolving I with three 3-dimensional $1^{st}$ order derivative of Gaussian functions of standard deviation $\sigma_{dog}$. Structure tensors were computed using MATLAB software (MathWorks, Inc.). Tractography and tractography visualization were performed using Diffusion Toolkit and TrackVis softwares ("http:" followed by "//trackvis." followed by "org/") respectively. In some cases, a principal fiber orientation may be defined as a tertiary eigenvector (i.e., with the smallest eigenvalue) of the structure tensor.

Quantification of Fiber-Like Structures

In some aspects, tractography methods of the present disclosure provide a plurality of streamlines that represent a fiber-like structure of a biological specimen obtained from a subject animal. The plurality of streamlines map onto fiber-like structures from, e.g., CLARITY images obtained from the biological specimen. In some cases, streamlines may be present in bundles, and the streamline count in each bundle tightly correlates with the ground-truth physical diameter of the corresponding bundles in a biological specimen. As used herein, "ground-truth" refers to information provided by direct observation, e.g., directly measured dimensions of a fiber-like structure. Quantification of the number of streamlines may be done by eye, or automatically by, e.g., software available in the art. The streamline count may also be used to measure the diameter of the fiber-like structure, the length of the fiber-like structure, and the size of the fiber-like structure. See examples section for detailed description of quantification of fiber-like structures of ArcTRAP labeled brains.

Screening Methods

The subject methods also provide a useful system for screening candidate therapeutic agents for their effect on a tissue or a disease. For example, a subject, e.g. a mouse, rat, dog, primate, human, etc. may be contacted with a candidate agent, an organ or a biopsy thereof may be prepared by the subject methods, and the prepared specimen microscopically analyzed for one or more cellular or tissue parameters. Parameters are quantifiable components of cells or tissues, particularly components that can be accurately measured, desirably in a high throughput system. A parameter can be any cell component or cell product including cell surface determinant, receptor, protein or conformational or post-translational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. Thus, for example, one such method may comprise detecting cellular viability, tissue vascularization, the presence of immune cell infiltrates, efficacy in altering the progression of the disease, etc. In some embodiments, the screen includes comparing the analyzed parameter(s) to those from a control, or reference, sample, e.g., a specimen similarly prepared from a subject not contacted with the candidate agent. Candidate agents of interest for screening include known and unknown compounds that encompass numerous chemical classes, primarily organic molecules, which may include organometallic molecules, inorganic molecules, genetic sequences, etc. Candidate agents of interest for screening also include nucleic acids, for example, nucleic acids that encode siRNA, shRNA, antisense molecules, or miRNA, or nucleic acids that encode polypeptides. An important aspect of the invention is to evaluate candidate drugs, including toxicity testing; and the like. Evaluations of tissue samples using the subject methods may include, e.g., genetic, transcriptomic, genomic, proteomic, and/or metabolomics analyses.

In some aspects, a screening method of the present disclosure screens a candidate agent for the ability to modulate the patterning of a fiber-like structure in a biological specimen of a subject animal using the subject methods to visualize the fiber-like structure. In some cases, the screening method may include: administering the candidate agent to the subject animal, isolating the biological specimen of the subject animal, and processing the biological specimen according to the subject methods to visualize a fiber-like structure. Any change in the patterning of a fiber-like structure in a biological specimen of a subject animal that has been administered a candidate agent, as compared to a fiber-like structure in a biological specimen of a subject animal that has not been administered any candidate agent (i.e., a control specimen), suggests that the candidate agent has the ability to modulate the patterning of a fiber-like structure. For example, a candidate agent may modulate the patterning of a fiber-like structure by, e.g., changing the direction of the trajectory of the fiber-like structure, increasing the volume of space occupied by the fiber-like structure, decreasing the volume of space occupied by the fiber-like structure, increasing the size of the fiber-like structure, decreasing the size of the fiber-like structure. In some cases, a change in the patterning of a fiber-like structure in a biological specimen of a subject animal may be detected by eye, or automatically, using visualization methods of the present disclosure. In some cases, a change in the patterning of a fiber-like structure may comprise an increased or decreased number of streamlines. A person of skill in the art would be able to recognize any changes to a fiber-like structure caused by administration of a candidate agent.

In some cases, a subject animal for use in a screening method may suffer from a pathological condition, wherein the pathological condition affects the patterning of a fiber-like structure of a biological specimen obtained from the subject animal. For example, the subject animal may have a neurological condition, e.g. Alzheimer's disease, Parkinson's disease, neuropathy, etc., that affects the patterning of a fiber-like structure of a biological specimen, e.g. brain, obtained from the subject animal. In some cases, the pathological condition may be a condition that affects the vasculature, e.g. venous thromboembolism, pulmonary embolism, deep vein thrombosis, a condition that affects the heart, e.g., a congenital heart defect. A subject animal with any pathological condition that may affect the patterning of a fiber-like structure of a biological specimen obtained from the subject animal may be used in the subject screening methods.

In some cases, a stimulant may first be delivered to a subject animal of the subject screening methods, wherein the stimulant has an effect on the patterning of a fiber-like structure of a biological specimen obtained from the subject animal. In such cases, screening a candidate agent includes screening for any candidate agents that increases or decreases the effect of the stimulant on the patterning of the fiber-like structure, as compared to a control that has not been exposed to the candidate agent. A stimulant that may be used in the subject screening methods includes amphetamine, caffeine, ephedrine, 3,4-methylenedioxymethamphetamine (MDMA), methylenedioxypyrovalerone (MDPV), prolintane, mephedrone, methamphetamine, nicotine, phenylpropanolamine, propylhexedrine, dimethylamylamine, pseudoephedrine, cathinone, cocaine, or any other stimulant known in the art, and any combinations thereof.

Systems

The present disclosure provides systems that may be used in practicing the subject methods. For example, systems of the instant disclosure may be used for visualizing a fiber-like structure of a biological specimen obtained from a subject animal. Systems include components required for generating a representation of a fiber-like structure from a CLARITY-based image of a biological specimen. In some aspects, such systems may include image processing circuitry configured to perform one or more of the subject visualization methods. In some cases, systems may include image capture and microscopy devices that perform image acquisition of a biological specimen. Systems of the present disclosure may include the above components, as well a processor in electronic communication with the components, and computer-readable medium with stored programming embodying algorithms required to carry out subject methods.

EXAMPLES

Materials and Methods:
Animals

Male and female C57BL/6J mice were group-housed on a reverse 12 h light/dark cycle. Mice were 6 to 8 weeks old at the time of viral infusion. Food and water were given ad libitum. Ai14 mice and wild type C57BL/6 mice were purchased from JAX. Rosa26$^{loxp-stop-loxp-eGFP-L10}$ (originally named TRAP (translating ribosome affinity purification); renamed to rTag here to differentiate from the other ArcTRAP used in this study (Targeted Recombination in Active Populations)) mice were from Dr. Evan Rosen at Harvard Medical School. Male mice were used in all behavioral assays. Both male and female mice were used for histology and anatomy assays. All experimental protocols were approved by the Stanford University Institutional Animal Care and Use Committee and were in accordance with the guidelines from the National Institutes of Health.

CAPTURE Labeling

Ai14 mice were injected with 1 µl mixture of AAV8-CaMKIIα-EYFP-NRN and AAV8-cFos-ER-Cre-ER-PEST in the left side of the mPFC. Two weeks after surgery, the mice were given 15 mg/kg cocaine (IP injection) or 20 random foot shocks (2 s, 0.5 mA, 2 shocks per minute on average) for two consecutive days. The control group remained in their home cage for the whole period. 10 mg/kg 4-hydroxytamaxofwas given to all mice 3 hours after the last behavior section to enable CreER-mediated recombination. The mice were returned to their home cage for additional 3-4 weeks to allow the full expression of fluorescence protein.

Stereotaxic Surgery 6-7-week-old mice were anaesthetized with 1.5-3.0% isoflurane and placed in a stereotaxic apparatus (Kopf Instruments). Surgeries were performed under aseptic conditions. A scalpel was used to open an incision along the midline to expose the skull. After performing a craniotomy, viruses (specific titer and volume for each virus can be found in the virus preparation section) was injected into the mPFC using a 10 µl nanofill syringe (World Precision Instruments) at 0.1 µl min-1. The syringe was coupled to a 33 gauge beveled needle, and the bevel was placed to face the anterior side of the animal. The syringe was slowly retracted 20 min after the start of the infusion. A slow infusion rate followed by 10 min of waiting before retracting the syringe was crucial to restrict viral expression to the target area. Infusion coordinates were: anteroposterior, 1.9 mm; mediolateral, 0.35 mm; dorsoventral, 2.6 mm. Coordinates for the unilateral implantation of fiber optic cannulas (Doric Lenses 200 µm diameter) were: anteroposterior, 1.9 mm; mediolateral, 0.35 mm; dorsoventral, −2.4 mm. All coordinates relative to bregma.

ArcTRAP Labeling

Male ArcTRAP (ArcCreER+/−, Ai14+/−) mice were used for study. 6-7 week old ArcTRAP mice were handled and injected with saline daily for at least 5 days prior to the experiment (including the home cage controls) to minimize the labeling due to handling and injections. The mice were 7-8 weeks old at the time of behavioral labeling. On experimental day 0, animals from both cocaine and shock groups were individually placed in a plastic chamber equipped with a grid floor connected to a shock generator, for 10 minutes to acclimatize the animals to the chamber (without receiving any actual shock or cocaine). On the following two days (experimental day 1 and day 2), animals were individually placed in the chamber for 10 minutes right after receiving 15 mg/kg intraperitoneal cocaine (cocaine group) or to receive 20 random foot shocks (2 s, 0.5 mA, 2 shocks per minute on average, shock group). The home cage control group remained in their home cage for the whole period. All the chambers were cleaned with 70% ethanol between trials. On experimental day 2, all mice received 5 mg/kg 4 TM (IP injection) 3 hours after the behavioral challenge to enable TRAP labeling. All groups, including the home cage controls, received 4-hyroxytamoxifen injections at the same time of the day (2-3 PM). The bedding of all cages were refreshed daily for 48 hours to prevent 4 TM retake. All the labeled mice were kept in their home cage for an additional 10 days to allow the full expression of tdTomoto before perfusion.

Activity-Dependent Ribosome Labeling

Male Arc-rTag mice were trained and labeled with 4 TM with the same protocol used in ArcTRAP labeling. After labeling, the mice were returned and kept in their home cage for 14 days to allow full integration of tagged ribosomes.

Delivery of 4-hydroxytamoxifen

An aqueous formulation (instead of oil, which tends to give slower drug release) is designed to facilitate transient 4 TM delivery. 10 mg of 4 TM (Sigma H6278) was first dissolved in 250 µl DMSO. This stock is first diluted in 5 ml of saline containing 2% Tween 80 and then diluted 1:1 again with saline. The final injectable solution contained: 1 mg/ml 4 TM, 1% Tween 80 and 2.5% DMSO in saline. The pharmacokinetics of 4 TM in mouse brain (using the above vehicle) was determined using a standard LS-MS method at Biomaterials and Advanced Drug Delivery Laboratory at Stanford. Briefly, 30 C57BL/6J mice were injected (IP) with 10 mg/kg 4 TM at indicated time points (n=5 each time point) and n=5 mice injected with vehicle alone were used as blank control. Brains were collected after perfusion using 1×PBS at different time points and snap-frozen in liquid nitrogen before homogenized for Liquid Chromatography Mass Spectrometry (LC-MS) analysis.

CLARITY Processing

The three key features of this new approach were: 1) accelerated clarification through parallelized flow-assisted clearing crucial for large cohorts (FIGS. 1D-1G) independent of specialized equipment such as electrophoresis or perfusion chambers; 2)>90% cost reduction (also important for these large behavioral cohorts) using a new refractive index-matching process; and 3) optical properties such that the whole mouse brain can be imaged using a commercial light-sheet microscope (LSM) under a single field of view (FOV) and as a single stack (~1200 steps across a ~6.6 mm range) in less than 2 hours with single-cell resolution throughout the whole volume (this speed and simplicity is also critical for large behavioral cohorts; FIGS. 2C-2D). Raw data files from each brain are ~12 GB in size and can be easily stored and directly analyzed on standard desktop workstations without the need for compression or stitching.

A hydrogel based on 1% acrylamide (1% acrylamide, 0.125% Bis, 4% PFA, 0.025% VA-044 initiator (w/v), in 1×PBS, Ref) was used for all CLARITY preparations. Mice were transcardially perfused with ice-cold 4% PFA. After perfusion, brains were post-fixed in 4% PFA overnight at 4° C. and then transferred to 1% hydrogel for 48 hours to allow monomer diffusion. The samples were degassed and polymerized (4-5 hours at 37° C.) in a 50 ml tube. The brains were removed from hydrogel and washed with 200 mM NaOH-Boric buffer (pH=8.5) containing 8% SDS for 6-12 hours to remove residual PFA and monomers. Brains could now be transferred to a flow-assisted clearing device using a temperature-control circulator or a simper combination of 50 ml tube and heated stirring plate (FIGS. 1D-1E). 100 mM Tris-Boric Buffer (pH=8.5) containing 8% SDS was used to accelerate the clearing (at 40° C.). Note that Tris-containing buffer should only be used after PFA is completely washed out as Tris has primary amide group that can potentially interact with PFA. With this setup, a whole mouse brain can be cleared in 12 days (with circulator, or 8 days for a hemisphere) or 16 days (with conical tube/stir bar). After clearing, the brain was washed in PBST (0.2% Triton-X100) for at least 24 hours at 37° C. to remove residual SDS. Brains were incubated in a refractive index matching solution (RapidClear, RI=1.45, Sunjin lab, "http://" followed by "www.sunjinlab" followed by ".com") for 8 hours (up to 1 day) at 37° C. and then 6-8 hours at room temperature. After the RC incubation, the brains were ready for imaging.

FIG. 1: Behavioral cohort-scale brainwide activity mapping. (FIG. 1A) Pharmacokinetics of 4 TM in mouse brain after a single intraperitoneal injection (10 mg/kg); n=5 per time point. (FIG. 1B) Cocaine dosing (15 mg/kg) and a series of foot shocks (0.5 mA/2 s) lead to place preference and aversion, respectively. An independent cohort of mice was used to validate the stimuli used in the study as appetitive (cocaine) and aversive (shock) using a 3-chamber place preference test. After two days of indicated exposure, fold-change in preference for the side where cocaine or shock was given was quantified. n=5 per group, *P<0.05, **P<0.01, unpaired t-test. Error bars, mean±s.e.m. (FIG. 1C) Representative movement tracking data. (FIG. 1D) Setup of parallel flow-assisted clearing. Up to 4 mouse brains can be inserted into a tissue cassette (30×40×12 mm). Two cassettes (indicated by red arrows) are inserted into a chamber constructed with an inlet and outlet for buffer exchange. To scale up clearing, multiple chambers (each containing up to 8 brains) can be connected in parallel to a temperature-controlled circulator (calibrated so that the temperature in the sample chamber is kept at 40° C.). (FIG. 1E) Alternative flow-assisted clearing setup without using a circulator. A 50 ml conical tube (with small holes drilled in the middle and on the bottom, as indicated by red arrows) can be inserted into a 250 ml glass bottle filled with clearing buffer. Each tube fits 3-4 mouse brains. Unidirectional flow (blue line) is created by using a magnetic stir bar and a stirring hot plate to accelerate the clearing. Upon first use, the temperature of the hot plate needs to be set properly so that the buffer temperature is maintained at desired level inside the conical tube. The speed of the stirring should also be set properly so that proper flow is being generated without damaging the sample. (FIGS. 1F-1G) Schematic and picture of the adapter used for mounting brains onto the ultramicroscope (Lavision Biotec). (FIG. 1H) Data processing pipeline for image registration, cell detection, annotation and quantification.

Figure 2:
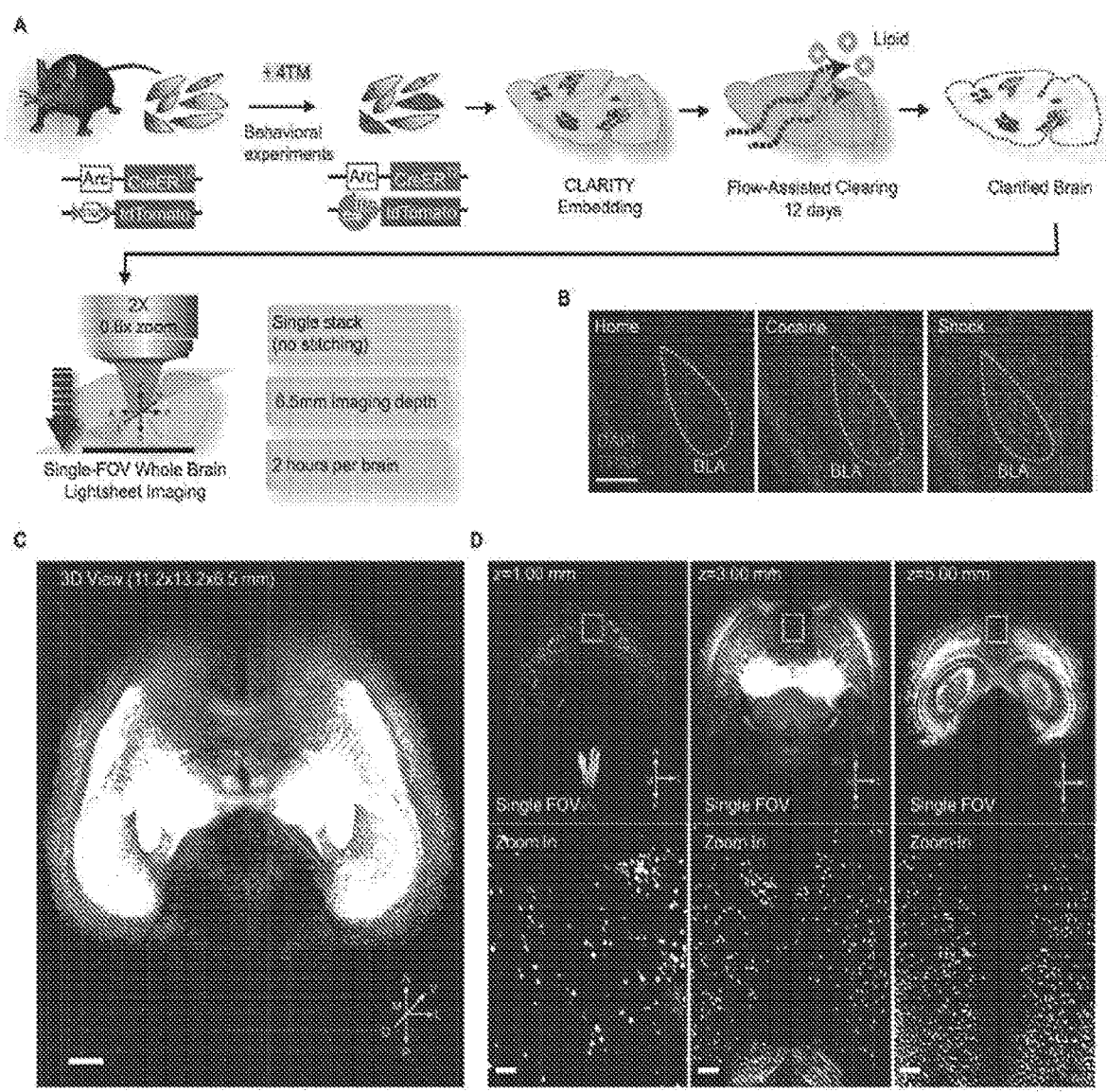
FIG. 2, panels A-D: Schematic showing an embodiment of a cohort-scale sample processing pipeline and images representing light-sheet microscopy images of processed brains.

FIG. 2: Behavioral cohort-scale brainwide activity mapping. (FIG. 2A) Schematic of ArcTRAP labeling and the enhanced cohort-scale CLARITY pipeline for rapid whole brain clearing and imaging. CreER expression is driven by the activity-dependent Arc promoter to mediate 4 TM-dependent recombination that permanently labels the active neurons with tdTomato. (FIG. 2B) Representative confocal images from 40 µm sections showing TRAP labeling in BLA (yellow circle). Scale bar: 400 µm. (FIG. 2C) Three-dimensional rendering of a CLARITY-processed whole mouse brain (ArcTRAP) imaged by LSM. Scale bar, 500 µm. (FIG. 2D) Top: single FOV images at indicated imaging depths. Bottom: zoomed in images from the yellow-boxed regions in the top row, showing cellular resolution. Scale bar, 100 µm.

Light-Sheet Imaging

Whole brain and hemisphere images were acquired with the Ultramicroscope II (Lavision Biotec). Samples were mounted to a custom 3D printed holder (FIGS. 1F-1G) using RapidClear Mounting Gel (Sunjin lab). For whole brains (TRAP brains), the brain was mounted with the ventral side on top. For hemisphere, the cut surface (midline of the brain) was placed in touch with the holder and with the most lateral part on the top. Samples were securely mounted to the holder after mounting gel solidified (~5 minute at 4° C.). Mounted samples were imaged inside an imaging chamber filled with 150 ml of Rapidclear (reusable by periodical filtering). Samples were left in imaging chamber for 20-40 min before imaging to allow the equilibrium of imaging liquid. Brains were imaged using a 2×/0.5 NA objective at 0.6× zoom (whole brain, TRAP) or 0.8× zoom (hemisphere, CAPTURE). Multi-color imaging was enabled by applying filters setting to a supercontinuum white laser (NKT photonics). Samples were with two light sheets (NA=0.144) illuminating from both sides of the sample. Z-step was set to 5.16 µm (at 0.6× zoom) or 4 µm (at 0.8× zoom). Five horizontal focal points were set to each imaging plane for creating a homogeneous field of view.

Image Processing and Visualization

All raw images were acquired as 16-bit TIFF files. The raw images were further processed by blind 3D deconvolution using AutoQuantX3 (Media Cybernetics). The parameters of the deconvolution were based on published methods using a similar light sheet microscope with a few modifications (Tainaka et al., Cell (2014) 159:911-924). Briefly, the modality was set to "Multi-photon fluorescence" 3D-blind deconvolution with 20 iterations. Noise was set to zero and using "unfiltered image" as "initial guess". In the expert settings, montage was turned on XY but off on Z, with 30-pixel overlap in XYZ. Other settings such as NA, spacing and magnitude were set based on the actual experiments. Either deconvolved or raw images can be 3D-rendered and visualized using Imarls (Bitplane, v8.1.2), for taking snapshot images and making movies.

Reconstruction and Analysis of Projections

Tractography methodology akin to what is used for diffusion MRI was used to reconstruct 3D models of fiber bundle trajectories based on the CLARITY data. The tractography algorithm (Mori et al., Annals of Neurology (1999) 45:265-269) propagates streamlines from a "seed" region through a vector field of voxel-wise principal fiber orientations and terminates if a streamline makes a sharp turn (angles larger than a prescribed threshold $\alpha_{thresh}$) or ventures outside of the masked region. For each voxel, the principal fiber orientation was estimated from a structure tensor, which was computed using the image intensity gradients (as a marker of the edges of fiber tracts) within a local neighborhood of the voxel (Bigun and Granlund, Proceedings of the IEEE First International Conference on Computer Vision (1987) 433-438; Budde and Annese, Frontiers in integrative neuroscience (2012) 7:3; Budde and Frank, NeuroImage (2012) 63:1-10; Kass and Witkin, Computer vision, graphics and image processing (1987) 37:362-385; Khan et al., NeuroImage (2015) 111:192-203; and Wang et al., Journal of biomedical optics (2015) 20:036003). The principal fiber orientation was defined as the tertiary eigenvector (i.e. with the smallest eigenvalue) of the structure tensor. The structure tensor was defined as:

$$S_w(p) = \iiint_{R^3} w(r) S_0(p-r) dr$$

where p and r represent spatial locations, w is a Gaussian weighing function with standard deviation $\sigma_g$, $S_0$ is a symmetric second-moment matrix derived from image intensity gradients:

$$S_0(p) = \begin{pmatrix} (I_x(p))^2 & I_x(p)I_y(p) & I_x(p)I_z(p) \\ I_y(p)I_x(p) & (I_y(p))^2 & I_y(p)I_z(p) \\ I_z(p)I_x(p) & I_z(p)I_y(p) & (I_z(p))^2 \end{pmatrix}$$

where $I_x$, $I_y$, and $I_z$ are the gradients of image intensity I along each of the x, y and z axes, computed by convolving/ with three 3-dimensional $1^{st}$ order derivative of Gaussian functions of standard deviation $\sigma_{dog}$. Structure tensors were computed using MATLAB software (MathWorks, Inc.). Tractography and tractography visualization were performed using Diffusion Toolkit and TrackVis softwares ("http:" followed by "//trackvis." followed by "org/") respectively.

Example 1: Resolving mPFC Populations and Projections Activated by Appetitive or Aversive Experience Similarity in activation pattern by appetitive and aversive experiences has been reported in individually-selected brain regions (verified broadly, though not in all regions, by the brainwide analysis conducted here). A falsifiable hypothesis arising from these observations would be that the same neuron type distribution was recruited by the two stimuli, for example reflecting neurons in each region reporting on arousal state due to the salience of the experience. In mPFC, other existing literature alone does not support or falsify this hypothesis, though mPFC is associated with specific reward and aversion processes (including cocaine-conditioned place preference on the one hand, as well as fear and anxiety behaviors on the other), in addition to more general functions potentially relevant to the single-population hypothesis (including attention, salience- and novelty-detection, and working memory). The region-specific differential activation detected by the brainwide analysis reported here may open the door to considering a distinct hypothesis at least for some circuits—that appetitive and aversive experience recruit distinct neuronal populations. Connectivity is one of the most important features that might resolve principal cell population types involved in such distinct processes, but this feature has been difficult to explore in a brainwide fashion while remaining linked (at the single-cell level) to function during behavior.

A very strongly-expressed activity-dependent cell-filling label (unlike traditional nuclear c-fos immunostaining or typical transiently or transgenically-expressed fluorophores) in principle might allow for acquisition of this crucial wiring information as well from the same experimental subjects, provided that axon tracts of labeled and filled neurons could be robustly imaged and quantified in this context. With the goal of building such a probe, a novel CLARITY-optimized axonal-filling enhanced fluorescent protein, engineered in part by inserting the 3' UTR of neuritin (NRN) RNA at the C-terminus of EYFP was developed. It was found that this DNA construct could be readily packaged into high-titer adeno-associated virus (AAV) capsids that indeed enabled focal injection-defined projection labeling in CLARITY; for example, efferent mPFC projections could be readily followed throughout the entire adult mouse brain after a single stereotaxic injection (FIGS. 3A-3B). Visualizing axonal tracks in 3D revealed key topographical features that were difficult, if not impossible, to detect in thin 2D sections (FIG. 3A, FIG. 4A); for example, a prominent axon bundle traveling from mPFC to ventral medial thalamus was observed to carry out a sharp U-turn near the VTA (FIGS. 3C-3D), a potentially important feature that has not been described in existing atlases (FIG. 4B).

Figure 3:
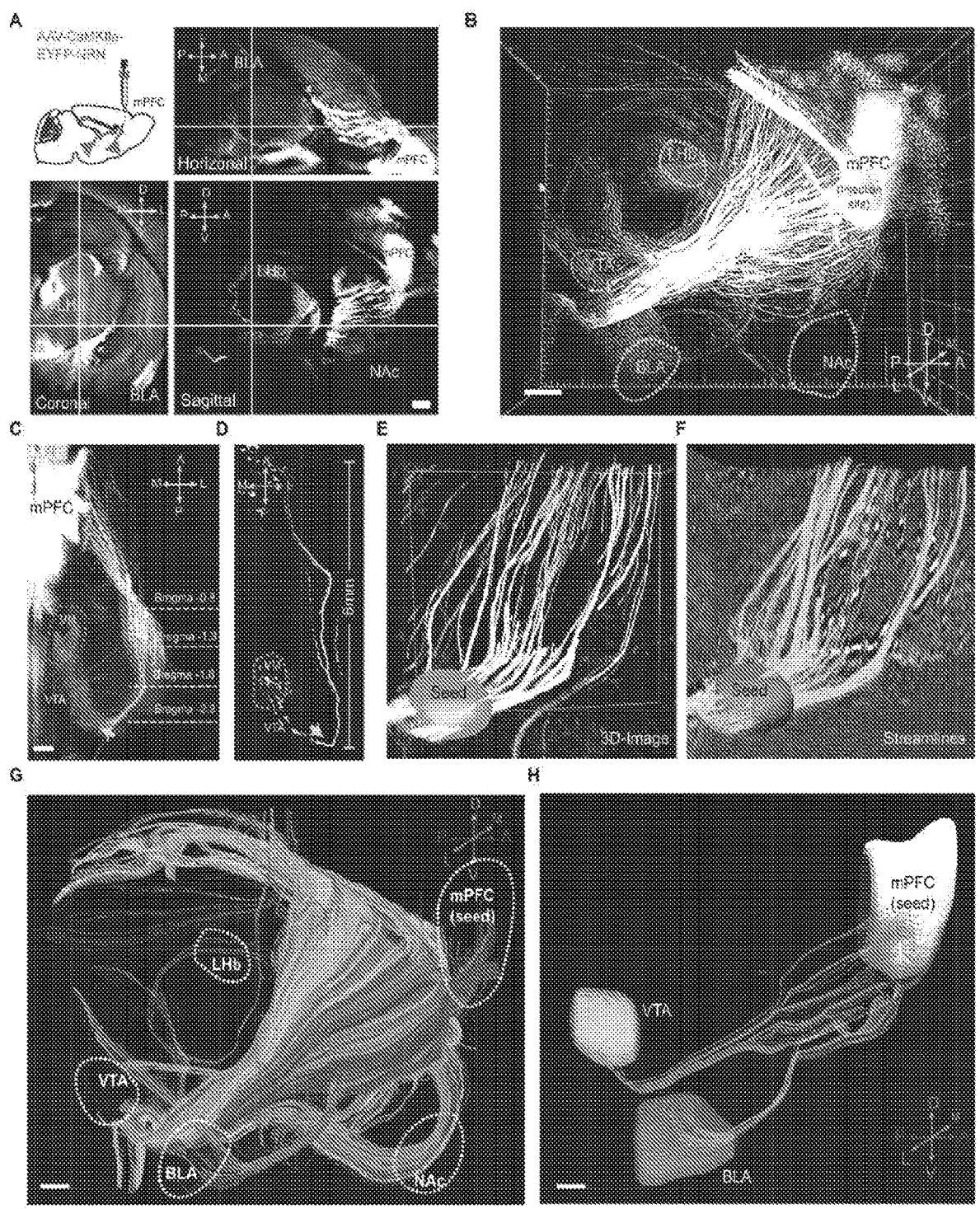
FIG. 3, panels A-H: Images demonstrating brain-wide origin/target-defined project mapping.

FIG. 3: CLARITY enables brain-wide origin/target-defined projection mapping. (FIG. 3A) 2D orthogonal views (horizontal, sagittal and coronal) of a mouse brain. Insert shows schematic for location of viral injection. Orientations: D: dorsal, V: ventral, A: anterior, P: posterior, L: lateral, M: medial. (FIG. 3B) Three-dimensional rendering of CLARITY hemisphere, visualizing outgoing mPFC projections (imaged by 2× objective at 0.8× zoom with a single FOV, step size: 4 µm, 1000 steps). (FIG. 3C) 3D visualization of the axonal bundle projecting from mPFC to VM, showing tracts turning near the VTA (indicated by arrows). (FIG. 3D) Visualizing the same projection in (FIG. 3C) with sparse labeling (using lower-titer virus). (FIG. 3E) Raw image from a CLARITY volume. Orange: user-defined "seed region" so that only the fibers passing this region were tracked. (FIG. 3F) Streamlines reconstructed from (FIG. 3E), using structural tensor-based tractography. Note that fibers in the CLARITY image that did not pass the user-defined seed region were excluded in the reconstruction (indicated by the magenta arrows). (FIG. 3G) Reconstructed brainwide streamlines from CLARITY image in (FIG. 3B). The streamlines are color-coded for orientation. A-P: red; D-V, green; L-M, blue. (FIG. 3H) Representative computational isolation of mPFC fibers that project to VTA (yellow) or BLA (green). All scale bars: 500 µm.

Figure 4:
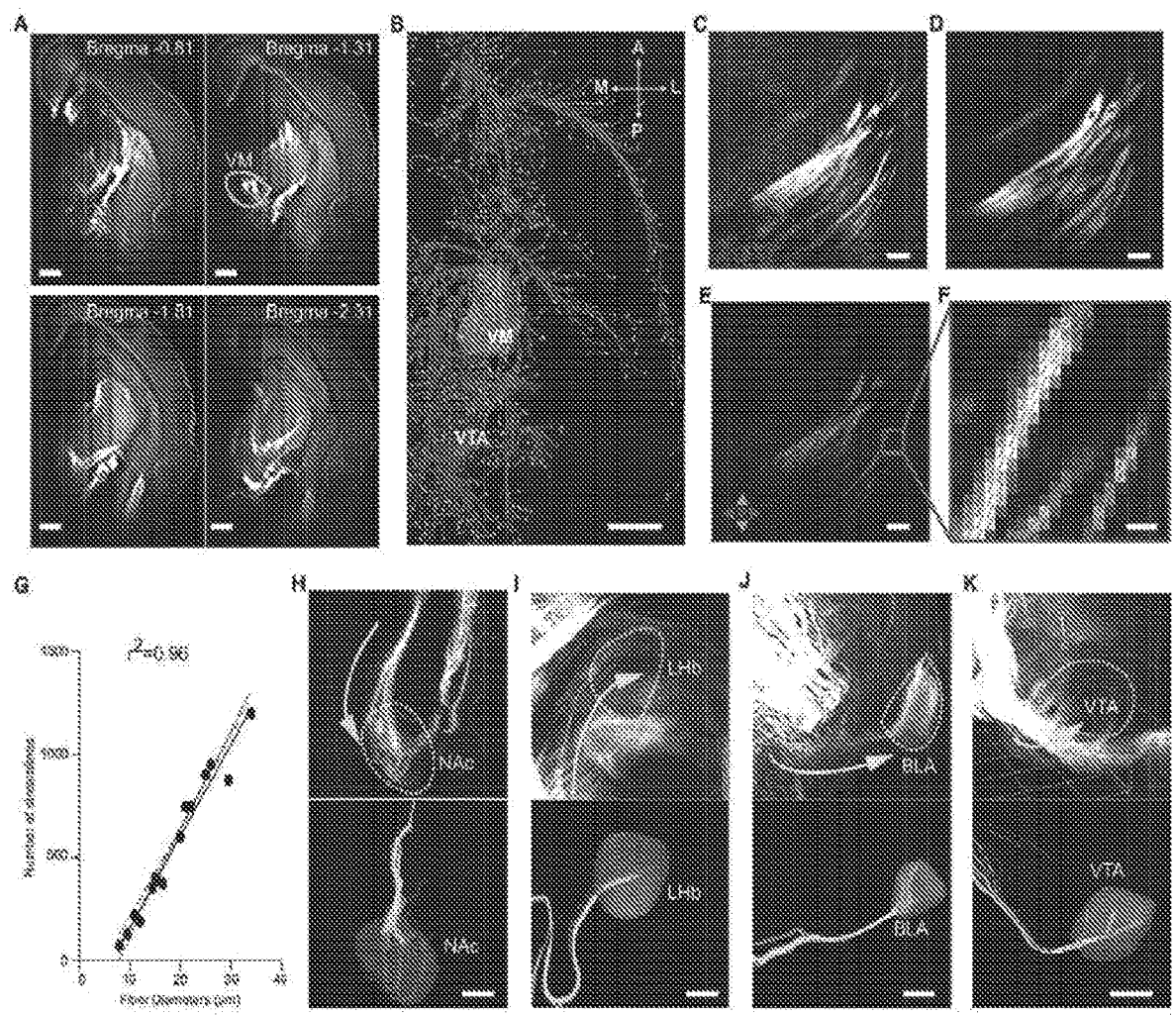
FIG. 4, panels A-K: Additional images demonstrating brain-wide origin/target-defined project mapping.

FIG. 4: CLARITY enables brain-wide origin/target-defined projection mapping. (FIG. 4A) 2D coronal sections (50 µm max-projection) at the indicated locations (relative to bregma). Scale bar: 500 µm. (FIG. 4B) A snapshot of putative mPFC to VM (highlight in green) projection paths (shown as red streamlines) from the Allen Brain mouse connectivity atlas ("http://" followed by "connectivity.brainmap" followed by ".org/"). Scale bar: 1 mm. (FIG. 4C-4F) Representative intermediate steps of reconstructing axonal projection to streamlines using structural tensor based CLARITY tractography. (FIG. 4C) Raw CLARITY image, showing outgoing mPFC projections (EYFP). (FIG. 4D) Image intensity gradient amplitude, computed by convolving the 3-dimensional CLARITY image volume with three 3-dimensional 1st order derivative of Gaussian functions ($\sigma dog=1$ voxel/6 µm) along each of the x, y and z axes. (FIG. 4E) Color-coded principal fiber orientations (A-P: red; D-V, green; L-M, blue), estimated as the tertiary eigenvectors of computed structure tensors ($\sigma d=1$ voxel/6 µm, $\sigma dog=1$ voxel/6 µm). For better visualization, the color brightness was weighted by the raw CLARITY image intensity. Scale bars: 100 µm. (FIG. 4F) A zoomed-in region of (FIG. 4E) showing the principal fiber orientations as color-coded vector fields overlaid on raw CLARITY image. The vectors are color-coded for their orientation. Scale bar: 6 µm. (FIG. 4G) Correlation between the diameter of each axonal bundle and the number of streamlines representing that specific bundle. The diameter was determined at the cross-sections of each bundle. The numbers of passing streamlines are also measured at the same cross-sections. n=15, Pearson correlation, $r^2=0.96$, P<0.0001. (FIGS. 4H-4K) Representative reconstructions of axonal projections (outgoing projections from mPFC) in various target regions: NAc (FIG. 4H), LHb (FIG.

4I), BLA (FIG. 4J) and VTA (FIG. 4K). Top row: CLARITY images; bottom row: reconstructed streamlines ending in the indicated 3D regions.

A method to compute 3D structure tensors from CLARITY images for tractography was developed in order to quantify tracts across large behavioral cohorts (FIGS. 4C-4F). Faithful reconstruction of calculated streamlines was achieved (using tools adapted from magnetic resonance image analysis for diffusion tractography); these streamlines mapped onto fibers from CLARITY images (FIGS. 3E-3F) and importantly, the streamline count in each bundle tightly correlated with the ground-truth physical diameter of the axonal bundles (FIG. 4G). Using this method, whole brain projections (originating from mPFC AAV injections) were reconstructed based on 3D CLARITY images (FIG. 3G); connectivity between a seed region (here defined by stereotaxic injection site) and any specified downstream target such as BLA or VTA, could be readily visualized and assessed by counting streamlines (FIG. 3H, FIGS. 4H-4K).

To integrate this new capability, with the needed additional capability of projection-labeling in cells defined by their use during behavioral experience, a viral CreER/4 TM strategy was developed to translate time-locked activity to sustained transgene expression (it was found that typical transgenic fluorophore expression driven by an activity-dependent promoter was, as expected, insufficiently strong for tractography). Therefore, a c-Fos promoter combining minimal promoter and regulatory elements in intron-1 was engineered (FIG. 5A) that was small enough to be packaged into AAV particles and specific enough to capture elevations in neuronal activity (FIGS. 5B-5D). A destabilized ER-Cre-ER-PEST cassette was also inserted under this promoter; when injected into the Ai14 reporter mouse, this viral CreER/4 TM system reliably enabled activity- and tamoxifen-dependent cell body and projection labeling (FIGS. 5E-5F).

Figure 5:
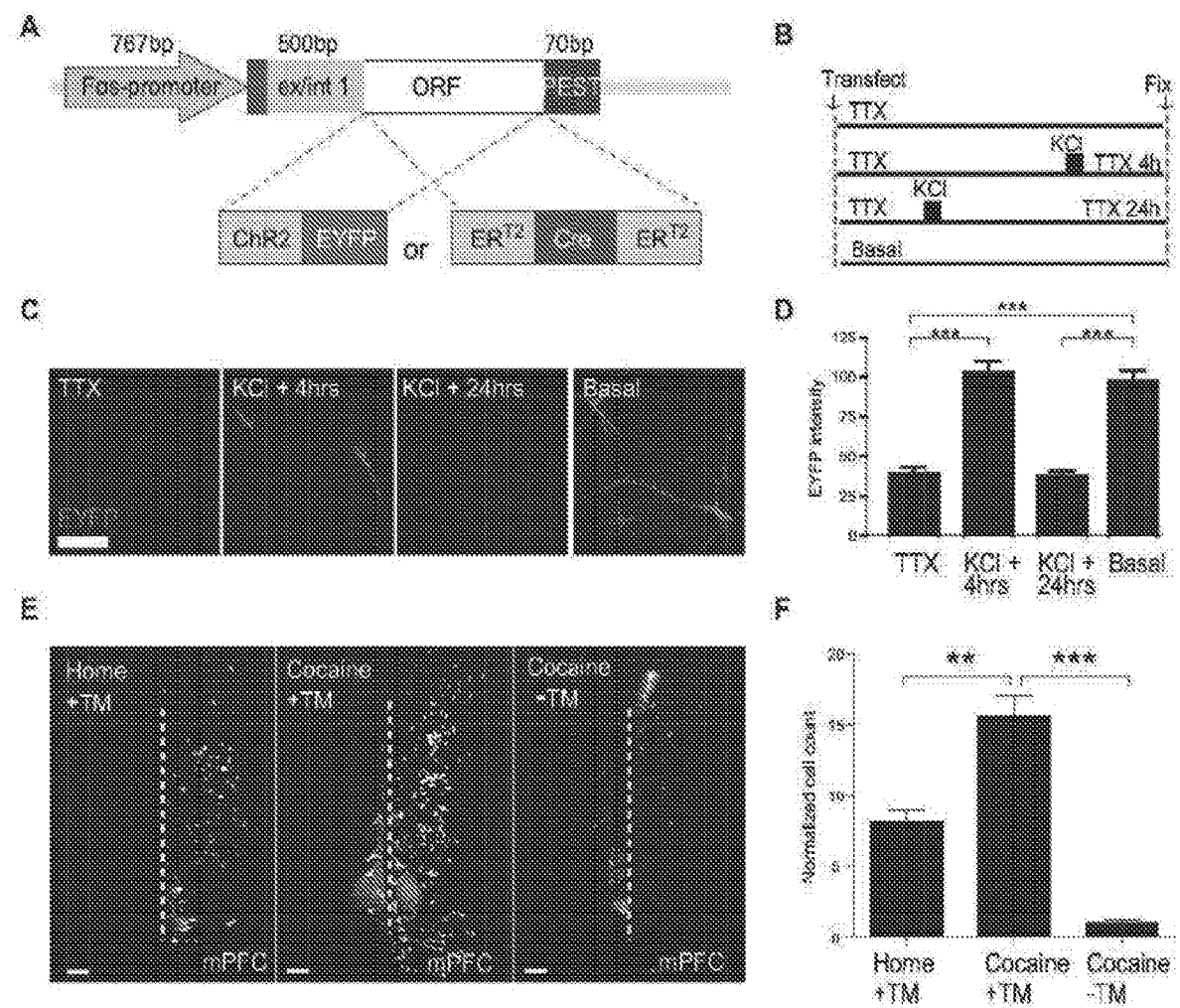
FIG. 5, panels A-F: Schematic showing the strategy of expression cassette construction, and data showing that cocaine and shock-activated mPFC populations have distinct projection targets.

FIG. 5: Distinct projection targets of cocaine and shock-activated mPFC populations. (FIG. 5A) Construction strategy. An expression cassette was inserted immediately after intron 1 of the c-fos gene. Either ChR2-EFYP (cFos-ChR2-EYFP, termed fosCh) or $ER^{T2}$-Cre-$ER^{T2}$ fusion was inserted, followed by a 70 bp PEST sequence to promote construct degradation (to further enhance specificity). (FIG. 5B) Schematic to illustrate treatment of cultured hippocampal neurons following transfection of c-Fos-ChR2-EYFP. Neurons were electrically silenced with TTX, APV and NBQX; fosCh expression was compared to expression levels in "basal" (spontaneously synaptically active, but not otherwise stimulated or silenced) cultures. Following a 30 min depolarizing stimulus (60 mM KCl) the TTX/APV/NBQX solution was replaced and groups were fixed at the indicated time points. (FIG. 5C) Representative images showing fosCh expression of cultured hippocampal neurons for each of the treatment groups. Scale bar: 25 μm. (FIG. 5D) Quantification of mean pixel intensity of EYFP expression for conditions represented in c, n=39-59 cells per group, $F_{3, 205}$=37.20, *$P<0.001$, ANOVA followed by Tukey's multiple comparison test. (FIGS. 5E-5F) AAV-cFos-$ER^{T2}$-Cre-$ER^{T2}$-PEST was injected into the mPFC of Ai14 Cre-reporter mice. The mice were divided into three groups (n=5 per group): home cage with 4 TM, cocaine-injected with 4 TM and cocaine-injected without 4 TM. (FIG. 5E) Representative images showing 4 TM-dependent and activity-dependent labeling of mPFC neurons (tdTomato+), scale bar: 100 μm. (FIG. 5F) Quantification tdTomato+ mPFC cells in three groups (normalized to the No-4 TM group). $P<0.01$, ***$P<0.001$, unpaired t-test. Error bars, mean±s.e.m.

A final essential feature (for behavioral cohort-wide quantitative activity-dependent projection mapping) was enablement of normalization on an individual-subject level to the absolute tract labeling strength independent of activity; this normalization is in principle crucial in a virus-based approach to control for variation in injection efficacy. This feature (FIG. 6A) was enabled by building in simultaneous two-color activity-independent (structural, EYFP) labeling and activity-dependent (tdTomato) labeling of projections from the same injection site. Dual-color quantification of projections across the intact brain to multiple downstream regions is then achieved by counting the number of streamlines ending in these regions, and the activity-dependence is corrected for anatomical and injection variability from the red/green streamline ratio. This quantification of projection use across the brain from behaviorally-defined neuronal populations is (for brevity) termed here CLARITY-based Activity Projection Tracking upon Recombination, or CAPTURE (FIG. 6A).

Figure 6:
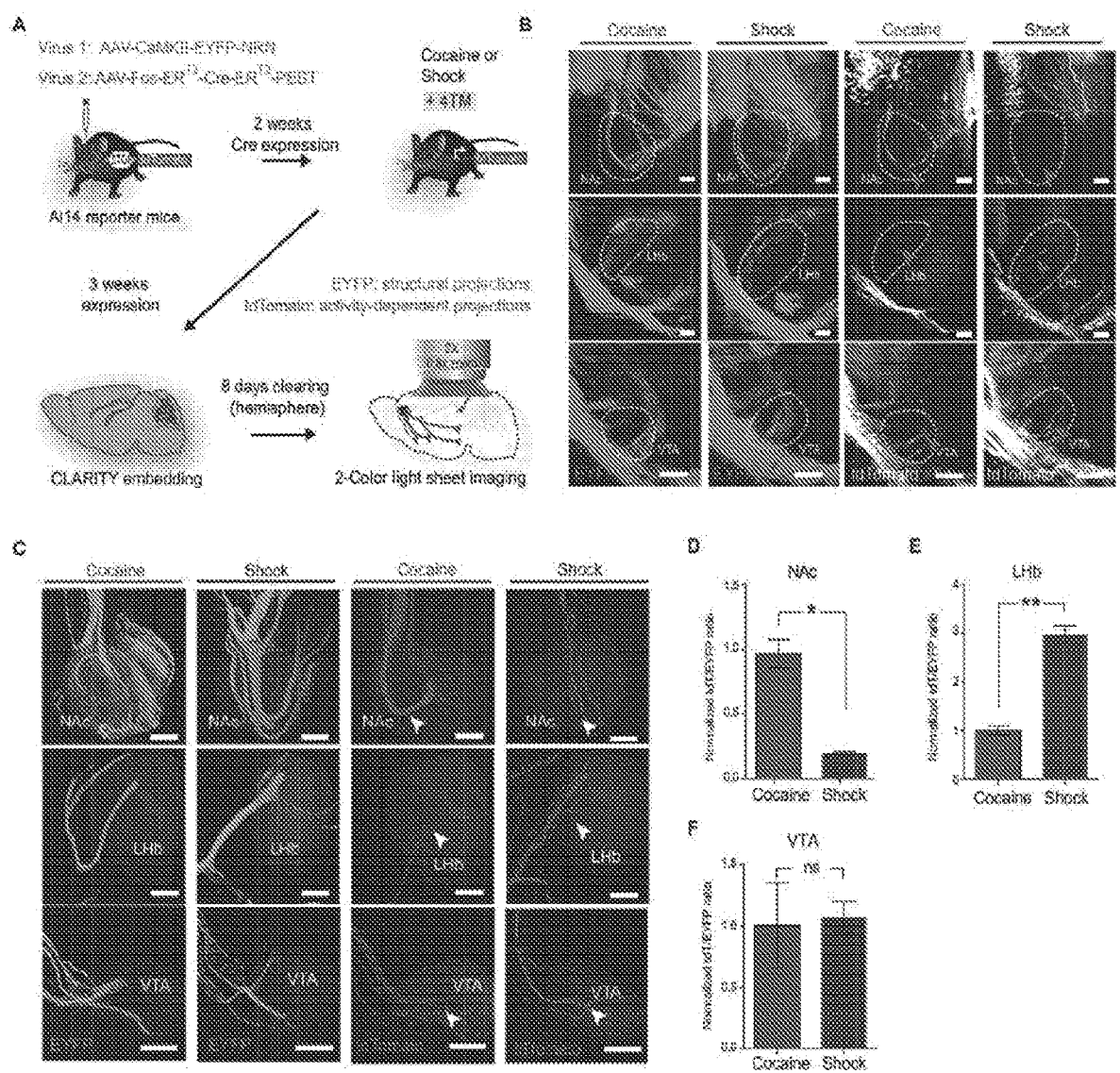
FIG. 6, panels A-F: Additional data showing that cocaine and shock-activated mPFC populations have distinct projection targets.

FIG. 6: Distinct projection targets of cocaine and shock-activated mPFC populations. (FIG. 6A) Summary of CAPTURE workflow (described in text). (FIG. 6B) Representative CLARITY images of the structural projections (green: EYFP) and activity-dependent projections (white: tdTomato) from cocaine- and shock-labeled mice in NAc (top row), LHb (middle row) and VTA (bottom row). Arrowheads indicate axon bundles terminating in the circled region. Scale bar: 200 μm. (FIG. 6C) Reconstructed streamlines from (FIG. 6B), showing streamlines terminating in the 3D brain regions (purple). Green streamlines: reconstructed from EYFP fibers; red streamlines: reconstructed from tdTomato fibers. Scale bars: 200 μm. (FIGS. 6D-6F) Quantification of projection intensity from cocaine- and shock-activated mPFC populations in three regions. Behavior-specific projection intensity was quantified using the ratio between red and green fibers (i.e. the number of red streamlines divided by the number of green streamlines) terminating in indicated 3D regions (NAc, LHb and VTA; n=6 per group; ns, $P>0.05$, *$P<0.05$, **$P<0.01$, unpaired t-test). Error bars, mean±s.e.m.

Example 2: Distinct Projection Patterns Among Behavioral Experience-Defined mPFC Populations CAPTURE was applied to quantify projections from cocaine- and shock-recruited mPFC populations. Two groups of Ai14 reporter mice were co-injected with CaMKIIα-EYFP-NRN and cFos-ER-Cre-ER-PEST AAVs, and subjected to 4 TM-mediated cocaine- and shock-labeling. With CAPTURE, projections from all CaMKIIα (principally excitatory glutamatergic) neurons are labeled with EYFP and projections from behaviorally-recruited populations are labeled with tdTomato. Importantly, EYFP fibers in the NAc, BLA and VTA were found to be indistinguishable between the cocaine- and shock-labeled animals, indicating minimal variation in viral injection, transduction, and expression between the two groups (FIG. 6B).

In the very same animals, significantly more projections from behaviorally-active mPFC neurons were observed targeting the NAc in cocaine-exposed animals compared to shock-exposed animals. Conversely, significantly more behaviorally-active mPFC fibers to the LHb in shock-exposed animals were observed (FIGS. 6C-6F). No significant difference in red/green (activity/structure) ratio was observed between the two groups in mPFC projections to the VTA, revealing no detectable systematic difference in efficiency or targeting of viral anatomical labeling. The cocaine-activated mPFC population thus preferentially projects to the NAc whereas the shock-activated population projects more strongly to LHb, revealing that the populations of neurons that are recruited in mPFC by distinct-valence behavioral experience are not simply different in terms of the patterns of input that they happen to receive, but represent anatomically distinct cell populations in terms of projection pattern across the brain.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for visualizing a fiber-like structure in a biological specimen, the method comprising:
    i) clearing the biological specimen comprising a fiber-like structure, wherein the fiber-like structure is detectably labeled;
    ii) illuminating the cleared biological specimen with two light sheets from a first side and a second side to produce an image volume, wherein the second side is opposite to the first side and wherein the image volume comprises a representation of the fiber-like structure;
    iii) defining a plurality of voxels within the representation of the fiber-like structure;
    iv) processing each of the plurality of voxels to estimate a plurality of principal fiber-like structure orientations; and
    iv) defining a starting point on the representation of the fiber-like structure and propagating a plurality of streamlines from the starting point, according to the plurality of principal fiber-like structure orientations, to visualize the fiber-like structure.

2. The method of claim 1, wherein processing each of the plurality of voxels comprises:
    a) identifying a plurality of image intensity gradients within a predetermined vicinity of the voxel;
    b) determining a structure tensor using the plurality of image intensity gradients; and
    c) estimating a principal fiber-like structure orientation from the structure tensor.

3. The method of claim 1, wherein the clearing comprises using a CLARITY-based method.

4. The method of claim 1, wherein the clearing comprises using an electrophoresis or perfusion-based method.

5. The method of claim 1, wherein the clearing comprises substantially removing a plurality of cellular components from the biological specimen.

6. The method of claim 1, wherein the clearing comprises substantially removing lipids from the biological specimen.

7. The method of claim 1, wherein each of the plurality of image intensity gradients indicate an edge of the fiber-like structure.

8. The method of claim 1, wherein each streamline of the plurality of streamlines terminates if a streamline makes a sharp turn.

9. The method of claim 8, wherein the sharp turn is at an angle larger than a predetermined threshold.

10. The method of claim 1, wherein each streamline of the plurality of streamlines terminates if the streamline propagates outside of a predetermined area.

11. The method of claim 1, wherein the principal fiber-like structure orientation is defined as a tertiary eigenvector of the structure tensor.

12. The method of claim 1, wherein the structure tensor is a three-dimensional structure tensor.

13. The method of claim 1, wherein the structure tensor is defined as a function comprising a Gaussian weighing function.

14. The method of claim 1, wherein the number of streamlines in the plurality of streamlines is used to measure a physical characteristic of the fiber-like structure.

15. The method of claim 1, wherein the number of streamlines in the plurality of streamlines is used to measure the diameter of the fiber-like structure.

16. The method of claim 1, wherein the number of streamlines in the plurality of streamlines is used to measure the size of the fiber-like structure.

17. The method of claim 1, wherein the biological specimen is a whole mammalian brain.

18. The method of claim 1, wherein the fiber-like structure is a neural projection.

19. The method of claim 1, wherein the fiber-like structure is a peripheral nerve.

20. The method of claim 1, wherein the fiber-like structure is a blood vessel.

21. The method of claim 1, wherein the biological specimen is a whole spinal cord.

22. The method of claim 1, wherein the detectably labeled fiber-like structure is labeled via stereotaxic injection.

23. The method of claim 1, wherein the detectably labeled fiber-like structure is labeled via genetic expression.

* * * * *